United States Patent [19]

Schmitt

[11] Patent Number: 5,208,229
[45] Date of Patent: May 4, 1993

[54] 2-(1,2,3-TRIAZOLYLSUBSTITUTED)PHENYL CARBAPENEM ANTIBACTERIAL AGENTS

[75] Inventor: Susan M. Schmitt, Scotch Plains, N.J.

[73] Assignee: Merck & Co., Inc., Rahway, N.J.

[21] Appl. No.: 859,599

[22] Filed: Mar. 23, 1992

Related U.S. Application Data

[63] Continuation of Ser. No. 793,270, Nov. 13, 1991, abandoned, which is a continuation of Ser. No. 619,647, Nov. 29, 1990, abandoned.

[51] Int. Cl.$^5$ .................... A61K 31/40; C07D 487/04
[52] U.S. Cl. ........................ 514/210; 540/302
[58] Field of Search ................. 540/302; 514/210

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,962,101 | 10/1990 | DiNinno et al. | 514/210 |
| 4,978,659 | 12/1990 | DiNinno et al. | 514/210 |

FOREIGN PATENT DOCUMENTS 0277743 8/1988 European Pat. Off. .

OTHER PUBLICATIONS

L. D. Cama, et al., Total Synthesis of Thienamycin Analogs-III, *Tetrahedron 39*, 2531 (1983).
R. N. Guthikonda, et al. Structure Activity Relationships in the 2-Arylcarbapenem Series, *J. Med. Chem.*, 30, 871 (1987).

*Primary Examiner*—Thurman K. Page
*Assistant Examiner*—Jyothsna Venkat
*Attorney, Agent, or Firm*—Richard C. Billups; Raymond M. Speer

[57] ABSTRACT

Carbapenems having the formula:

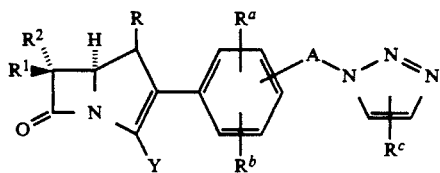

are useful antibacterial agents.

13 Claims, No Drawings

2-(1,2,3-TRIAZOLYLSUBSTITUTED)PHENYL CARBAPENEM ANTIBACTERIAL AGENTS

This is a continuation of application Ser. No. 07/793,270, filed Nov. 13, 1991 now abandoned, which is a continuation of Ser. No. 07/619,647, filed Nov. 29, 1990 now abandoned.

BACKGROUND OF THE INVENTION

The present invention relates to antibacterial agents of the carbapenem class, in which the 2-position sidechain is characterized by a phenyl moiety, optionally substituted, to which is attached, usually through an alkyl bridge, a 1,2,3-triazolyl group, optionally substituted, with attachment being only through a nitrogen atom of the triazolyl group, as described in more detail below.

Thienamycin was an early carbapenem antibacterial agent having a broad spectrum; it has the following formula:

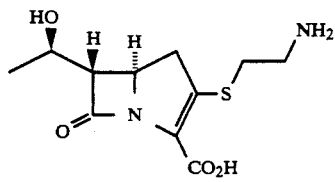

Later, N-formimidoyl thienamycin was discovered; it has the formula:

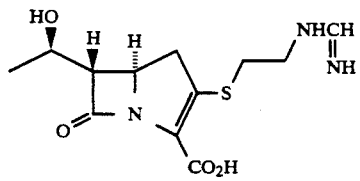

The 2-(1,2,3-triazolyl substituted)phenyl carbapenems of the present invention have an antibacterial potency equal to or greater than, in most cases, that of either thienamycin or N-formimidoyl thienamycin. The compounds of the present invention are also more resistant than thienamycin or N-formimidoyl thienamycin to degradation by the dehydropeptidase enzyme DHP-I, thus permitting greater therapeutic application of the compounds.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

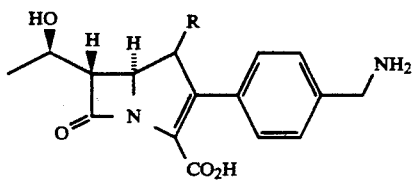

However, these compounds belong to a different class from those of the present invention and are distinguished by different physiological properties.

There is also described in EP-A-0 277 743 a particular class of carbapenems of the formula:

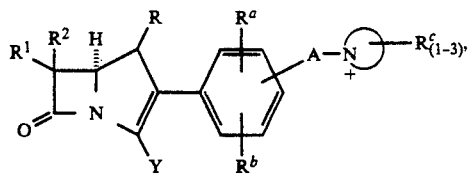

but the disclosure thereof is very limited and none of those compounds suggest the compounds of the present invention.

SUMMARY OF THE INVENTION

The present invention provides novel carbapenem compounds of the formula I:

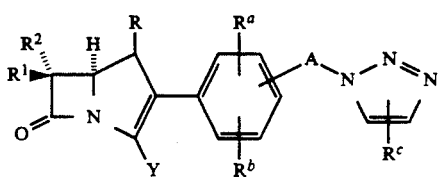

wherein:

R is H or $CH_3$;

$R^1$ and $R^2$ are independently H, $CH_3$—, $CH_3CH_2$—, $(CH_3)_2CH$—, $HOCH_2$—, $(R)$—$CH_3CH(OH)$—, $(CH_3)_2C(OH)$—, $FCH_2$—, $F_2CH$—, $F_3C$—, $(R)$—$CH_3CH(F)$—, $CH_3CF_2$—, or $(CH_3)_2C(F)$—;

$R^a$ and $R^b$ are independently hydrogen or:
  a) a trifluoromethyl group: —$CF_3$;
  b) a halogen atom: —Br, —Cl, —F, or —I;
  c) $C_1$-$C_4$ alkoxy radical: —$OC_{1-4}$alkyl, wherein the alkyl is optionally mono-substituted by $R^q$, where $R^q$ is a member selected from the group consisting of —OH, —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);
  d) a hydroxy group: —OH;
  e) a carbonyloxy radical: —O (C=O)$R^s$, where $R^s$ is $C_{1-4}$ alkyl or phenyl, each of which is optionally mono-substituted by $R^q$ as defined above;
  f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)—, —$S(O)_2$—or —$NR^3$—, to form a ring (where $R^e$ is hydrogen, $C_1$-$C_4$alkyl, and $C_1$-$C_4$alkyl mono-substituted with $R^q$ and the ring is optionally mono-substituted with Rq as defined above);
  g) a sulfur radical: —$S(O)_n$—$R^s$ where n=0–2, and $R^s$ is defined above;

h) a sulfamoyl group: —SO$_2$N(R$^y$)R$^z$ where R$^y$ and R$^z$ are as defined above;

i) azido: N$_3$ j) a formamido group: —N(R$^5$)(C=O)H, where R$^t$ is H or C$_{1-4}$ alkyl, and the alkyl thereof is optionally mono-substituted by R$^q$ as defined above;

k) a (C$_1$-C$_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;

l) a (C$_1$-C$_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;

m) a ureido group: —N(R$^t$)(C=O)N(R$^y$)R$^z$ where R$^t$, R$^y$ and R$^z$ are as defined above;

n) a sulfonamido group: —N(R$^t$)SO$_2$R$^2$, where R$^s$ and R$^t$ are as defined above;

o) a cyano group: —CN;

p) a formyl or acetalized formyl radical: —(C=O)H or —CH(OCH$_3$)$_2$;

q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

r) carbonyl radical: —(C=O)R$^s$, where R$^s$ is as defined above;

s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;

t) a (C$_1$-C$_4$ alkoxy)carbonyl radical: —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N(C$_1$-C$_4$ alkoxy)-carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)R$^z$ where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^b$)$_2$]; alkylphosphono {P=O(OM$^b$)—[O(C$_1$-C$_4$ alkyl)]}; alkylphosphinyl [P=O(OM$^b$)—(C$_1$-C$_4$alkyl)]; phosphoramido P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each heteroatom has both of its attached hydrogen atoms replaced by one oxygen thus forming a carbonyl moiety and there are one or two carbonyl moieties present in the ring;

ad) C$_2$-C$_4$ alkenyl radical, optionally monosubstituted by one of the substituents a) to ac) above and phenyl which is optionally substituted by R$^q$ as defined above;

ae) C$_2$-C$_4$ alkynyl radical, optionally monosubstituted by one of the substituents a) to ac) above;

af) C$_1$-C$_4$ alkyl radical;

ag) C$_1$-C$_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to ag) above;

R$^c$ is R$^a$ as defined hereinabove, hydrogen, —NR$^y$R$^z$ (where R$^y$ and R$^z$ are defined hereinabove), or

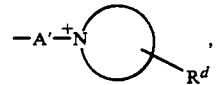

but independently selected from R$^a$ and from each other if more than one R$^c$ is present, and is attached to a ring carbon atom or a ring nitrogen heteroatom the valency of which is not satisfied by the ring bonds;

R$^d$ is R$^a$ as defined hereinabove, hydrogen or —NR$^y$R$^z$ (where R$^y$ and R$^z$ are defined hereinabove),

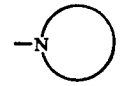

is a 5- or 6-membered monocyclic aromatic heterocycle or an 8-, 9- or 10-membered bicyclic aromatic heterocycle, the heterocycle containing a first nitrogen in an aromatic 5- or 6-membered first ring, with said first nitrogen quaternary by virtue of attachment to A' in addition to the ring bonds thereto, with attachment of the heterocycle to A' by way of said first nitrogen atom, with the first ring containing zero or one of either of the atoms of O or S, with the first ring containing zero to two additional nitrogen atoms, with the first ring optionally fused to a 3- or 4-membered moiety to form the optional second ring, with the moiety containing at least one carbon atom, with the moiety containing zero or one of either of the atoms of O or S, with the moiety containing zero to two nitrogen atoms, and with the moiety being saturated or unsaturated and the second ring aromatic or non-aromatic;

A and A' are independently $(CH_2)_m$—Q—$(CH_2)_n$, where m is zero to 6 and n is zero to 6 and Q is a covalent bond, O, S, SO, $SO_2$, NH, —$SO_2NH$—, —$NHSO_2$—, —CONH—, —NHCO—, —$SO_2N$(-$C_1$-$C_4$alkyl)—, —$N(C_1$-$C_4$alkyl)$SO_2$—, —CON(-$C_1$-$C_4$alkyl)—, —$N(C_1$-$C_4$alkyl)CO'—, —CH=CH—, —CO—, —OC(O)—, —C(O)O— or $N(C_1$-$C_4$alkyl); provided when m=n=zero that Q is not a covalent bond;

Y is selected from:
  i) COOH or a pharmaceutically acceptable ester,
  ii) $COOR^3$ wherein $R^3$ is a readily removable carboxyl covering group which is not a pharmaceutically acceptable ester,
  iii) COOM wherein M is an alkali metal, or
  iv) COO—;
  provided that when Y is other than iv) and a quaternary nitrogen heteroatom is present, a counterion $Z^-$ is provided, or the pharmaceutically acceptable salt thereof.

The $R^a$, $R^b$ and $R^c$ substituents optionally represent from 1 to 2 substituents which may be the same or different and are selected on an independent basis While a single such substituent is clearly preferred, there is occasion to use up to three such substituents, e.g., where it is desired to enhance the effect of a particular substituent group by employing multiple substituents. Thus, two carboxymethyl substituents may be used. At other times it may be desired to employ a substituent known to enhance antibacterial activity of the overall molecule against a particular bacterium, for example, while also employing a substituent known to improve the duration of action of the overall molecule.

The overall molecule must be electronically balanced. Since a quaternary nitrogen may be present in the compounds of the present invention, a balancing anion must, in that case, also be present. This is usually accomplished by having Y be $COO^-$. However, where Y is, e.g., a pharmaceutically acceptable ester, and a quaternary nitrogen is present, a counterion (anion) $Z^-$ must be provided, or alternatively, an anionic substituent might be utilized Further, it is within the scope of this invention to utilize an anionic substituent where the quaternary nitrogen is already balanced by Y=$COO^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "heteroatom" means N, S, or O, selected on an independent basis.

Under the definition of "Y", the term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug. Since the compounds of the present invention may be carboxylates, the salts would be cations such as benzathine, chloroprocaine, choline, diethanolamine, meglumine and procaine. The metallic cations such as aluminum, calcium, lithium, magnesium and zinc are potential choices. The alkali metal cations sodium and potassium are specifically defined. It will also be noted that the compounds of the present invention are potentially internal salts or zwitterions, since under physiological conditions the carboxyl group may be anionic, and this electronic charge might then be balanced off internally against the cationic charge of a quaternary nitrogen atom. Where this is not the case, and a quaternary nitrogen heteroatom is present, it is provided in the definition of "Y" that a counterion "$Z^-$" is present. This counterion is selected from the group of suitable pharmaceutical anions, e.g., chloride, phosphate and tartrate.

The term "readily removable carboxyl covering group" means a conventional substituent which takes the place of the acidic hydrogen of the carboxyl group and thereby prevents said group from reacting with any of the reagents employed in the various steps of the overall synthesis. Such covering of the carboxyl group is often necessary to prevent unwanted competing reactions involving said carboxyl group from taking place. Thus, all of these compounds are intermediates. The conventional covering substituent must also be "readily removable", by which is meant that it is selectively removable, i.e., it is not likely to be removed during the course of ordinary procedures which are to be carried out on the carbapenem nucleus and sidechains, while, on the other hand, it is likely to be removed by procedures which are not so harsh as to disturb the basic ring structure of the carbapenem nucleus or unprotected substituents thereon.

It is preferred that when one of $R^1$ or $R^2$ is H, the other is (R)'$CH_3CH(OH)$— or (R)—$CH_3CH(F)$—, and (R)—$CH_3CH(OH)$— is most preferred. Further, it is preferred that the configuration at C-6 is (S), and that at C-5 is (R).

Representative A groups are —$CH_2$—, —$CH_2CH_2$—, —$CH_2$—$N(CH_3)$—, —$CH_2$—S—, —$CH_2$—S—$CH_2$—, and —$CH_20(C=O)$—.

Representative $R^c$ groups are —$CH_3$, —$CH_2CH_3$, —$(CH_2)_3CH_3$, —$OCH_3$, —$SCH_3$,

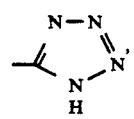

—COOH, —$NHCH_2COOH$, —OH, —$CH_2OH$, —$CH_2COOH$, —$CH_2CH_2COOH$, —$CH_2CONH_2$, —$CH_2CH_2S^+(CH_3)2$, —$CH_2CH_2SO_3H$,

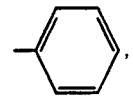

—CONH₂, —SO₂NH₂, —SO₃H, —NH₂, —N(CH₃)₂, —CON(CH₃)₂, —NHCH₃, —CH₂NH₂, —CN, —CH₂CN, —CH₂SCH₃, —CH₂SO₃⁻, —CH₂SOCH₃, —CH₂SO₂CH₃, —SO₂CH₃, —SOCH₃, —CH₂OCH₃, —CH₂P(O)(OH)OCH₃, —CF₃, —CH₂OC(O)NH₂, —CH₂SO₂NH₂, —SCH₂CH₂CN, Br, Cl, F, —SCF₃, —CH₂SCF₃, and —SCH₂CF₃.

The aromatic heterocycle moiety has been conveniently represented throughout by the following formula:

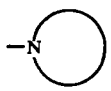

Useful examples of the nitrogen-containing aromatic heterocycle moiety are set out below.

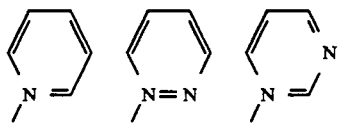

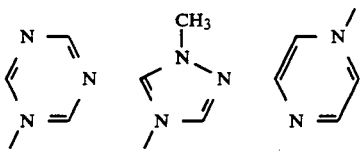

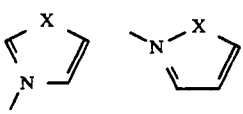

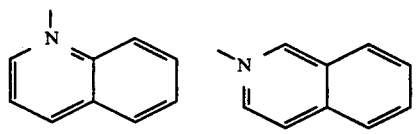

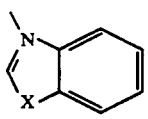

where X = O, S, or NR₄;
R₄ = Me, CH₂CN, CH₂CONH₂, CH₂CH₂⁻, CH₂SO₃⁻.

The pyridyl group is preferred since it provides the desired properties of good antibacterial spectrum and potency combined with chemical stability and satisfactory resistance to hydrolysis by the dihydropeptidase (DHP-I) enzyme, together with ready availability and ease of handling as a starting material. However, any of the other groups set out above, as well as those falling within the definition of the heteroaryl moiety set out herein but not specifically described above, are also suitable, although perhaps in some cases less desirable in terms of one or more of the criteria mentioned above. With regard to all of the preferred substituents described above, the following compounds are preferred embodiments of the present invention.

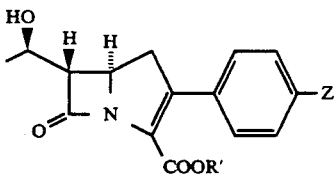

Where Z is:

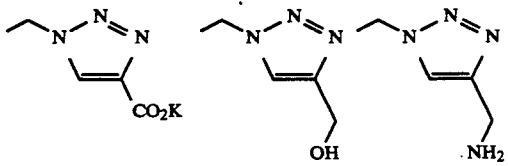

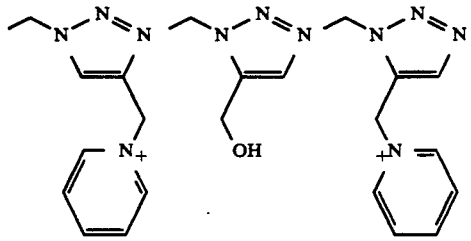

where R' is a negative charge — or an alkali metal salt, a pharmaceutically acceptable carboxy covering group, or additionally a readily removable carboxyl covering group which is not a pharmaceutically acceptable carboxy covering group.

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above include non-toxic acid addition salts The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may also take the form where Y is $COOR^3$, where $R^3$ is a readily removable carboxyl protecting group. Such conventional blocking groups consist of known ester groups which are used to protectively block the carboxyl group during the synthetic procedures described further below. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing agents under mild conditions, and catalytic hydrogenation. Examples of such ester protecting groups include benzhydryl, p-nitrobenzyl, 2-naphthylmethyl, allyl, benzyl, trichloroethyl, silyl such as trimethylsilyl, phenacyl, p-methoxybenzyl, acetonyl, o-nitrobenzyl, 4-pyridylmethyl, and $C_1$-$C_6$ alkyl such as methyl, ethyl or t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 timer per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1 1. A preferred DHP inhibitor is 7-(L-2-amino-2-carboxyethylthio)-2-(2,2-dimethylcyclopropanecarboxamide)-2-heptenoic acid or a useful salt thereof.

DETAILED DESCRIPTION OF THE INVENTION

The 2-(1,2,3-triazolyl substituted)phenyl carbapenem compounds of the present invention may be prepared in accordance with well known procedures in the art. Particularly useful are the following synthetic schemes in which the symbols R, $R^1$, $R^2$, $R^a$, $R^b$, $R^c$, $R^d$, $R^e$, A, and 

are as defined above.

Scheme A shows the synthetic steps leading to the intermediate A5. A benzene moiety, optionally substituted with $R^a$, $R^b$ or suitable precursor substituents thereof, may be added to azetidin-2-one A1 in a Grignard reaction. The Grignard reaction requires that the Grignard reagent A2 be prepared by reaction of the corresponding bromobenzene derivative and magnesium with 1,2-dibromoethane initiation in a suitable polar aprotic solvent, such as THF, diethyl ether, or the like, from 20° C. to 60° C., and subsequently contacting the Grignard reagent (A2) with A1 in a suitable polar aprotic solvent, such as THF, diethyl ether, or the like, at from $-70°$ C. to about 20° C. to produce azetidin-2-one A3. Alternatively, the bromobenzene may be reacted with t-butyllithium, n-butyllithium, or the like in a suitable polar aprotic solvent, such as THF, diethyl ether, or the like, at from $-78°$ to $-50°$ C. followed by the addition of magnesium bromide to produce the same Grignard reagent A2. $R^i$ of A1 is in practice pyrid-2-yl but may clearly be a variety of substituents including aromatic and heteroaromatic substituents. Further $R^i$ might be for example phenyl, 2-pyrimidinyl or 2-thiazolyl.

Azetidin-2-one A3 is an intermediate that may be ring closed to a carbapenem. It is on this intermediate that $R^a$, $R^b$ or precursor substituent such as -butyldimethylsilyloxy-methyl may be modified where such modification is incompatible with the carbapenem nucleus. For example, a convenient reaction to remove the t-butyldimethylsilyl group of A3 is to expose it to a 2% solution of sulfuric acid in methanol at 0° C. for from a few minutes to several hours. Flow Sheet A (continued) shows the resulting compound A4. If a t-butyldimethylsilyl group were removed by exposing carbapenem A5 to tetra-n-butylammonium fluoride and acetic acid in THF, a substantial portion of carbapenem would be degraded and lost. Thus, modification of the precursor substituent in this instance and replacement with another precursor substituent or even -A-heterocycle is optionally performed before the intramolecular cyclization is carried out, provided the substituent is uncharged.

Compound A3 or A4 may be ring closed to carbapenem A5 by refluxing in xylene with a trace of p-hydroquinone for about 1 to 2 hours in an inert atmosphere. It is on this intermediate A5 that final elaboration to generate the -A-triazole moiety from a precursor substituent, e.g. hydroxymethyl, may be accomplished, as will be described in detail hereinbelow. Removal of the protecting groups by methods known in the art, such as a palladium (0) catalyzed deallylation, then provides the final compound Formula I. Such final elaboration and deprotection is described in further detail below.

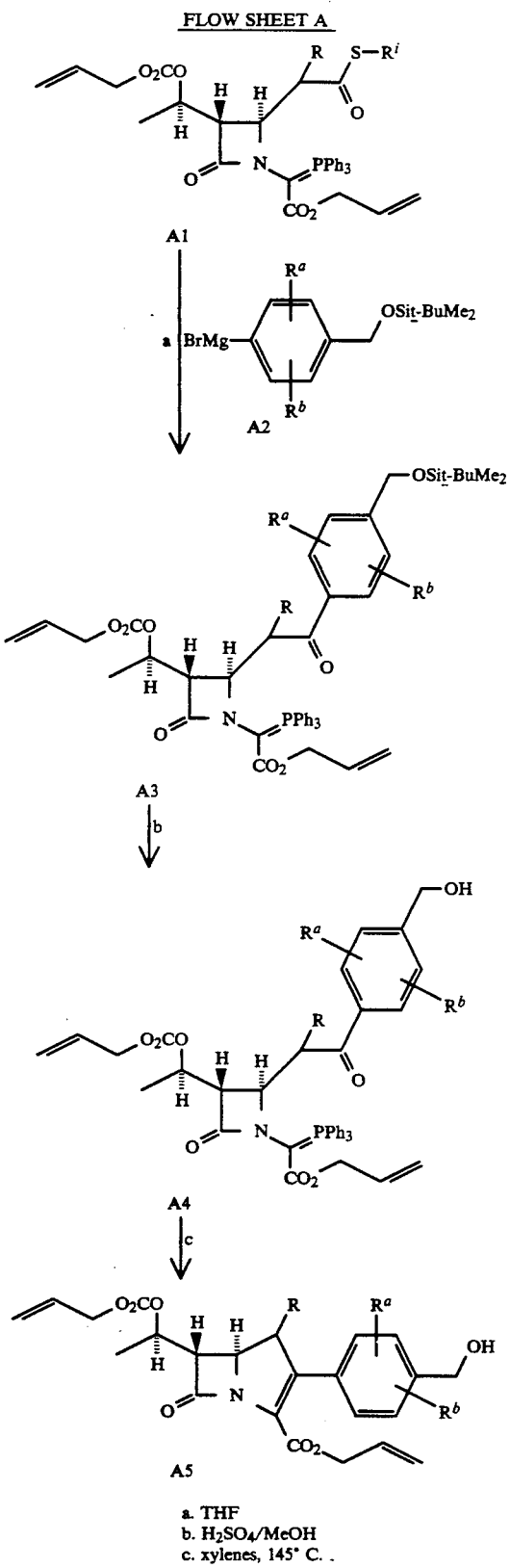

FLOW SHEET A a. THF
b. $H_2SO_4$/MeOH
c. xylenes, 145° C.

Flow Sheet B shows an alternative synthesis of an intermediate functionally equivalent to A5, i.e. attach-

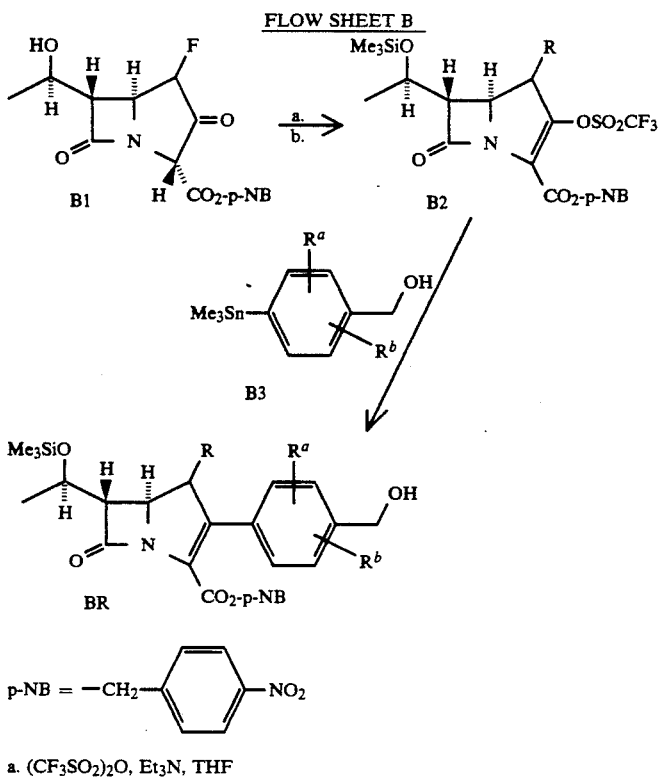

FLOW SHEET B p-NB = —CH$_2$—C$_6$H$_4$—NO$_2$ a. (CF$_3$SO$_2$)$_2$O, Et$_3$N, THF
b. TMS—OTf cross-coupling reaction between a carbapenem triflate and a suitably substituted arylstannane, a process which is described in U.S. Pat. application Ser. No. 485,096 filed Feb. 26, 1990. Thus the 2-oxocarbapenem B1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as methylene chloride or tetrahydrofuran, at a reduced temperature, such as −78° C. An organic nitrogen base, such as triethylamine and the like, is then added to the reaction solution followed immediately by a silylating agent, such as trimethylsilyl trifluoromethanesulfonate to provide intermediate An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, the stannane B3 and, optionally, a suitably substituted phenylphosphine, such as tris(4-methoxyphenyl)phosphine, tris(2,4,6-trimethoxyphenyl)phosphine and the like. A halide source, such as lithium chloride, zinc chloride or diisopropylammonium chloride and the like, is added and the reaction solution is quickly warmed to a suitable temperature, such as 0° to 50° C., and allowed to stir for a suitable amount of time. The carbapenem B4 is obtained by conventional isolation/purification methodology known in the art. Final elaboration of the -A-heterocycle moiety from a precursor substituent, e.g. hydroxymethyl, may be accomplished on carbapenem intermediate B4. Removal of protecting groups then provides the final compound of Formula I. Such final elaboration and deprotection is described in further detail below.

Scheme C shows the synthetic steps leading to the intermediate C2 which incorporates the triazole group characteristic of the instant invention. The scheme, which shows the synthesis wherein A is —CH$_2$—, is illustrative and is not meant to be limiting. Thus, the intermediate A5 may be reacted with hydrogen azide in the presence of diethyl azodicarboxylate and triphenylphosphine in a suitable polar aprotic solvent, such as tetrahydrofuran (THF), diethyl ether, or the like, at from 0° to 20° C. to provide the azidocarbapenem C1. Alternatively, the hydroxyl group of A5 can be converted to a leaving group, such as a mesylate or iodide, which can then be reacted with an azide source, such as lithium azide or sodium azide to provide the azidocarbapenem C1 (as described in U.S. Pat. No. 4,543,257). The intermediate C1 is then contacted with a suitable substituted acetylene, such as allyl propiolate, propargyl alcohol, propargyl chloride and the like, in a suitable solvent, such as benzene, toluene, xylene and the like, at from 80° to 150° C. to provide the triazolylmethylphenylcarbapenem C2. The substituent R$^t$ on the triazole ring may be R$^c$ or may be further elaborated as described in detail hereinbelow to provide R$^c$. Removal of the protecting groups by methods known in the art, such as a palladium(O) catalyzed deallylation, then provides the final compound of Formula I. Such deprotection is described in further detail below.

SCHEME C

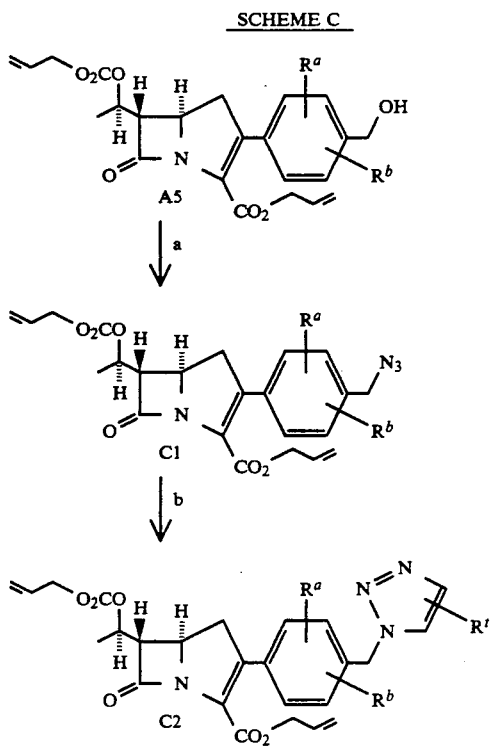

a. HN₃/DEAD/Ph₃P/benzene/Et₂O
b. H—C≡C—R$^i$/benzene/reflux

Azetidin-2-one A1 (R$^i$=2-pyridyl), a pyridyl-thio-ester, is a well known compound in the Production of carbapenems. Diverse synthetic schemes useful to make A1 may be imagined by the skilled artisan. Particularly useful to the instant invention is a synthetic scheme set out further in Flow Sheet D below in which the symbol R$^i$ is as defined above. The steps for preparing intermediate A1 are analogous to the procedures described, for example, in U.S. Pat. Nos. 4,260,627 and 4,543,257; L. D. Cama et al., *Tetrahedron,* 39, 2531 (1983); R. N. Guthikonda et al., *J. Med. Chem.,* 30, 871 (1987).

FLOW SHEET D

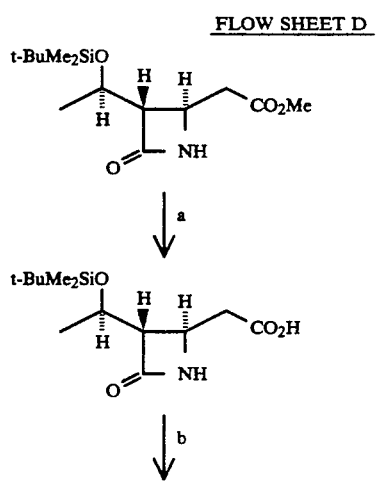

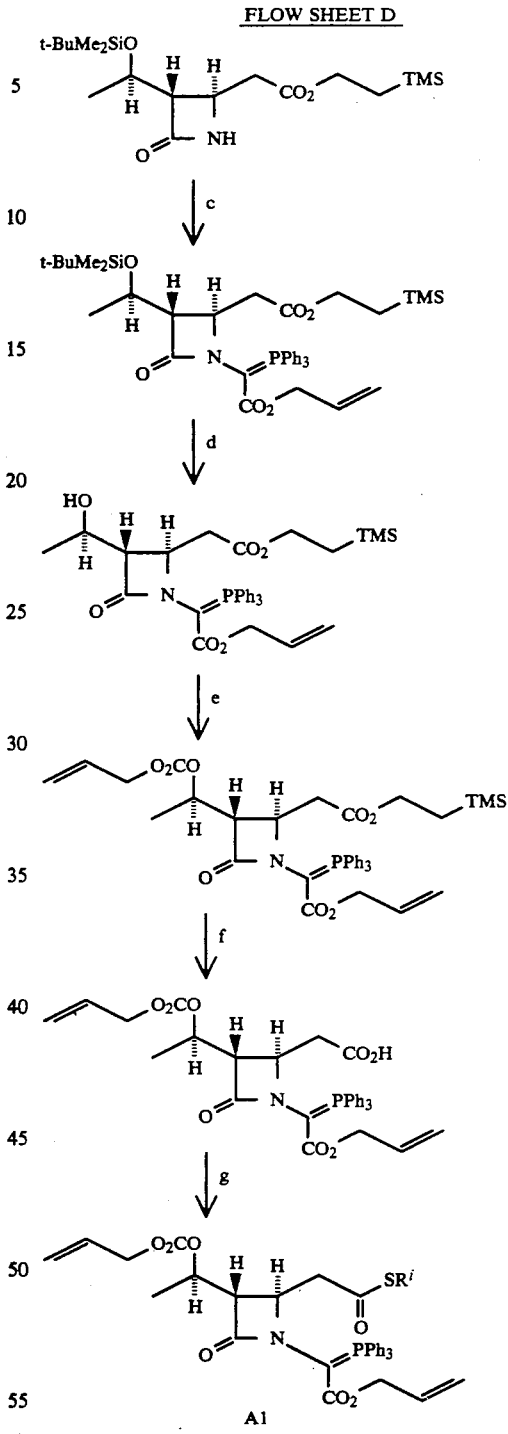

a. NaOH/MeOH
b. carbonyl diimidazole

60  HO⁀TMS c. OHCCO₂⁀ ;

65  SOCl₂;
    Ph₃P
d. 6N HCl/MeOH

-continued
FLOW SHEET D e. ClCO₂  ; DMAP f. nBu₄NF
g. R$^i$—SS—R$^i$, Ph₃P 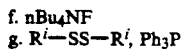

The R$^c$ substituents herein are intended to represent suitable further substituents on the triazole moiety, and optional heterocycle substituent. As seen above, the heterocycle moieties are monocyclic or bicyclic aromatic groups containing heteroatoms. Given this class of primary substituent, further suitable substituents may be readily discovered in the penem and carbapenem art. For example, suitable substituents for heterocycle moieties are generally taught in U.S. Pat. No. 4,729,993 assigned to Merck and Co. or in U.S. Pat. No. 4,746,736 assigned to Bristol-Myers Co.

Broadly, when two R$^c$'s are present they may be the same or different and may be selected on an independent basis from the group as defined above. While a single such substitution is preferred, there is occasion to use up to two such substituents on a triazole moiety, where it is desired to enhance the effect of a particular substituent group by employing multiple substituents. The particular choice of R$^c$ will depend upon the situation. For instance, a specific R$^c$ may lend particular stability to a nitrogen cation on a heterocycle moiety. At other times it may be desired to employ a substituent known to enhance antibacterial activity of the overall molecule against a particular bacterium, for example, while also employing a substituent known to improve some other property such as water solubility or the duration of action of the overall molecule.

Preferred R$^c$ substituents attached to ring carbon atoms are —NH₂, —SCH₃, —SOCH₃, —CH₂OH, —CH₂NH₂, —(CH₂)₂OH, —OCH₃, —COOM$^b$, —CH₂COOM$^b$, —CH₂CH₂COOM$^b$, —CH₂SOCH₃, —CH₂SCH₃, —CH₂O(C=O)NH₂, —CHO, —CH₂—(-heterocycle aromatic ring), —SO₃M$^b$, —CH₂SO₃M$^b$, —CH₂CH₂SO₃M$^b$, —CH₂Br, —CH₂Cl, —CH₂F, —CH₂I, —CH₃, CH₂CH₃, CH₂CONH₂ and CH₂CON(C₁-C₄alkyl where M$^b$ is defined above.

It is preferred that the triazole moiety and optional heterocycle moiety have no more than two R$^c$ substituents which are other than hydrogen. The previously listed more specific structures should be interpreted to have no more than two R$^c$ substituents for each monocyclic group.

Suitable A spacer moieties include —CH₂—, —CH₂CH₂—, —CH₂CH₂CH₂—, —CH₂CH₂CH₂CH₂—, —OCH₂CH₂—, —SOCH₂—, —SO₂CH₂—, —SCH₂CH₂—, —SOCH₂CH₂—, —SO₂CH₂CH₂—, —NHCH₂CH₂—, —N(CH₃)CH₂CH₂—, —CH₂N(CH₃)CH₂CH₂—, —CONHCH₂CH₂—, —SO₂NHCH₂CH₂—, —COCH₂—, —CH=CHCH₂— and —CH₂OCH₂CH₂—. Preferably, where Q is O, S, NH or N(C₁₋₄alkyl), then n is 2–6 and m is as previously described.

Conveniently, the triazole moiety should be synthesized with a precursor substituent which may be elaborated into the desired cationic substituent. The identity of the precursor substituent will vary according to the particular R$^c$ desired. For example, one such precursor substituent is hydroxymethyl.

Such a hydroxymethyl precursor substituent may be elaborated into the -A'-heterocycle moieties by converting the hydroxyl into an active leaving group such as an iodide followed by reaction with a desired nitrogen containing aromatic compound. More particularly, two alternative procedures may be utilized to produce a leaving group on the precursor to moiety -A'-heterocycle and subsequently to replace such a leaving group with moieties of the type just described.

For a first procedure, the hydroxyl group of the precursor substituent may be converted to a methanesulfonate group by treating with methanesulfonyl chloride in the presence of triethylamine. A suitable solvent, e.g., dichloromethane, is employed, and the reaction is carried out at reduced temperatures. In turn, the methanesulfonate intermediate may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. The iodide is then reacted in a nucleophilic displacement reaction with an aromatic compound which has a nucleophilic side-chain substituent such as mercapto or amino. In this displacement reaction, it is the side-chain substituent that is the reacting nucleophile and not the aromatic ring nitrogen. Suitable substrates for this reaction include 2-(mercaptomethyl)pyridine, 2-aminopyridine, 2-(aminomethyl)-pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation as described above then gives the cationic heterocycle substituent.

For a second procedure, the hydroxyl group of the precursor substituent may be converted into the reactive trifluoromethanesulfonate (triflate) group. However, such an activating group may not be isolable by conventional techniques. In such a case, the activating group may be formed and used in situ. Thus, treatment of the hydroxyl group with trifluoromethanesulfonic (triflic) anhydride in the presence of a hindered, non-nucleophilic base such as 2,6-lutidine, 2,4,6- collidine, or 2,6-di-tert-butyl-4-methylpyridine in a suitable solvent, such as dichloromethane, at reduced temperatures provides the triflate activating group. Alternatively, the iodide described above may be treated in situ with silver trifluoromethanesulfonate in a suitable solvent such as acetonitrile at reduced temperatures to provide the triflate activating group. The triflate is then treated as described hereinabove for the iodide.

Where the cationic substitution has a substituent R$^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The steps for preparing the 2-phenyl carbapenem intermediate are well known in the art and are explained in ample detail in U.S. Pat. Nos. 4,260,627 and 4,543,257.

In the preparation methods described above, the carboxyl group at the 3-position remains blocked by a carboxyl covering group until the final product is prepared. Then, if the anionic carboxylate is desired so as to form a zwitterionic internal salt, deblocking may be carried out in a conventional manner, with care being taken to avoid a procedure which is so harsh as to disrupt other portions of the final product molecule.

The general synthetic description above and the particular examples which follow show the 6-(1-hydroxyethyl) moiety, which is preferred in most cases. However, it has been found that with certain 2-sidechain selections, the ultimate balance of favorable biological properties in the overall molecule may be enhanced by selection of the 6-(1-fluoroethyl) moiety instead. Preparation of this and other 6-fluoroalkyl compounds within the scope of the present invention may be carried out in a straightforward manner using techniques well know in the art of preparing carbapenem antibacterial compounds. See, e.g., J. G. deVries et al., *Heterocycles*, 23 (8), 1915 (1985); BE 900 718 A (Sandoz).

The invention is further defined by reference to the following examples, which are intended to be illustrative and not limiting. All temperatures are in degrees Celsius. For $^1$H-NMR spectra run in CDCl$_3$, tetramethylsilane (TMS) was used as an internal standard, and chemical shifts are expressed in ppm downfield from TMS. In the case of spectra run in D$_2$O, no internal standard was used; the DOH peak was assigned at 4.80 ppm.

EXAMPLE I

Dipotassium (5R,6S)-2-[4-(4'-carboxylate-1',2', 3'-triazol-1'-ylmethyl)phenyl]-6-[1R-hydroxyethyl]-carbapen-2-em-3-carboxylate and Dipotassium (5R, 6S)-2-[4-(5'-carboxylate-1',2', 3'-triazol-1'-ylmethyl)phenyl]-6-[1R-hydroxyethyl]-carbapen-2-em-3-carboxylate

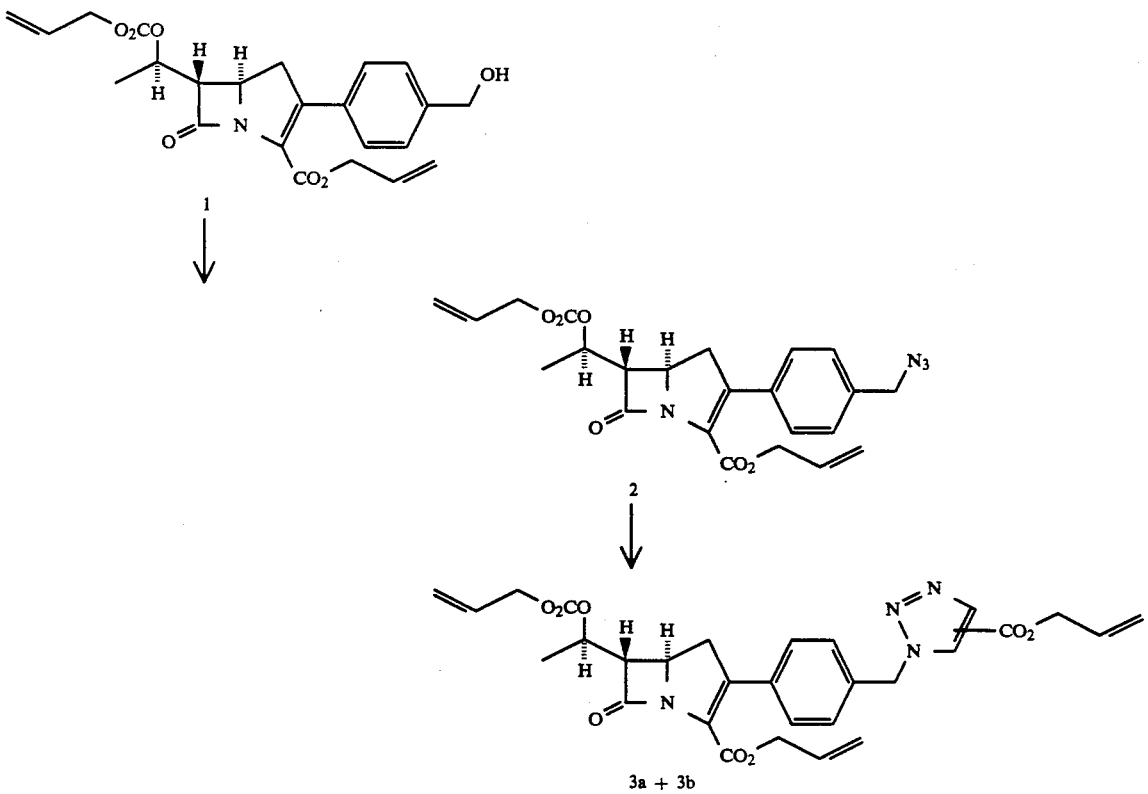

Step A: Allyl (5R,6S)-2-(4-azidomethylphenyl)-6-[1R-(allyloxycarbonyloxy)ethyl]carbapen-2-em-3-carboxylate 2

To a solution of 265 mg (0.62 mmol) of carbapenem 1 and triphenylphosphine (192 mg, 0.73 mmol) in 6.8 mL of ether at 0° C. was added simultaneously diethyl azodicarboxylate 107 μL, 0.68 mmol) and 0.44 mL of a solution of hydrogen azide in benzene (ca. 0.68 mmol) [prepared from sodium azide and sulfuric acid in a water/benzene mixture]. The solution was stirred for 5 minutes at 0° C. At the end of this time the light yellow solution was treated with 13 mL of 0.5M pH7 phosphate buffer. The layers were separated, and the aqueous layer was extracted with ether. The combined ether layers were then dried over MgSO$_4$, filtered and concentrated under vacuum. The residue was purified by thin layer chromatography (6–1000μ silica gel plates; 5% EtOAc in CH$_2$Cl$_2$) to provide 215 mg (77% yield) of the title compound 2.

$^1$H-NMR (300 MHz, CDCl$_3$): 1.49 (d, J=6 Hz, CH$_3$CHO—), 3.19 (dd, J=10, 18 Hz, H$_{1a}$), 3.29 (dd, J=8, 18 Hz, H$_{1b}$), 3.42 (dd, J=3, 8Hz, H$_6$), 4.29 (m, H5), 4.35 (s, CH$_2$N$_3$), 4.59–4.76 (m, CO$_2$CH$_2$), 5.12–5.40 (m, CH$_3$CHO · and CH=CH$_2$), 5.79–6.01 (m, CH=CH$_2$), 7.30, 7.38 ppm (2d, phenyl protons).

IR (CH$_2$Cl$_2$) 2120 (N$_3$), 1780 (β-lactam carbonyl); 1740 and 1725(other carbonyls)cm-1.

Step B:
Allyl-(5R,6S)-2-[4-(4'-(allyloxycarbonyl)-1',2',3'-triazol-1'-ylmethyl)phenyl]-6-[1R-(allyloxycarbonyloxy)ethyl]-carbapen-2-em-3-carboxylate and Allyl-(5R,6S)-2-[4-(5'-(allyloxycarbonyl)-1',2',3'-triazol-1'-ylmethyl)phenyl-6-[1R-(allyloxycarbonyloxy)ethyl]carbapen-2-em-3-carboxylate To a solution of 88 mg (0.19 mmol) of the azidocarbapenem 2 from Step A in 1.8 mL of benzene was added 700 μL of allyl propiolate (7 mmol) [prepared as described by C. D. Heaton, *J. Am. Chem. Soc.*,71, 2948 (1949)]. The reaction solution was stirred at room temperature (RT) for 4 days, then concentrated under vacuum. The residue was partitioned between methylene chloride and an aqueous $K_2HPO_4$ solution. The separated aqueous layer was extracted with methylene chloride, and the combined methylene chloride layers were washed with brine. The methylene chloride layer was then dried, filtered and concentrated under vacuum.

The residue was purified by thin layer chromatography (2-1000μ silica gel plates; 1:1 EtOAc: hexanes) to provide 77 mg (72% yield) of one of the regioisomers 3a and 15 mg (14% yield) of the other regioisomer 3b.

3a $^1$H-NMR (200 MHz, $CDCl_3$): δ1.48 d, J=6 Hz, $CH_3CHO$—), 3.18 (dd, J=10, 18Hz, $H_{1a}$), 3.30 (dd, J=9, 18 Hz, $H_{1b}$), 3.43 (dd, J=3, 8Hz, $H_6$), 4.30 (m, $H_5$), 4.57–4.88 (m, $CO_2CH_2$), 5.09–5.46 (m, $CH_3CHO$ and CH=$CH_2$), 5.58 (s,—$CH_2$—triazole), 5.76–6.12 (m, CH=$CH_2$), 7.27 and 7.39 (2d, phenyl protons), 8.0 ppm (s, triazole proton).

3b $^1$H-NMR (200 MHz, $CDCl_3$): δ1.47 (d, J=6Hz, $CH_3CHO$—), 3.15 (dd, J=10, 18 Hz, $H_{1a}$), 3.27 (dd, J=9, 18 Hz, $H_{1b}$), 4.21 (dd, J=3, 8Hz, $H_6$), 4.27 (m, $H_5$), 4.55–4.80 (m, $CO_2CH_2$), 5.11–5.43 (m, $CH_3CHO$ and CH=$CH_2$), 5.73–6.06 (m, CH=$CH_2$); 5.91(s on top of previous m, —$CH_2$—triazole), 7.31 (s, phenyl protons), 8.15 ppm (s, triazole proton).

IR ($CH_2Cl_2$) 1775 (β-lactam carbonyl), 1740 and 1720 (other carbonyls)cm-1.

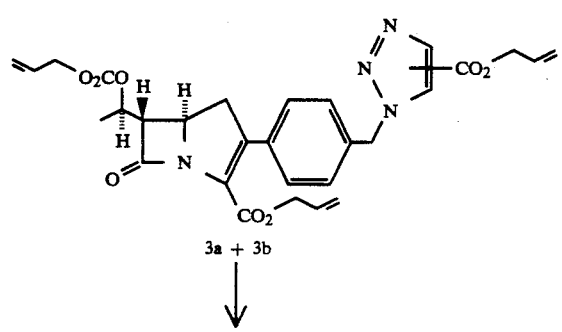

3a + 3b

↓

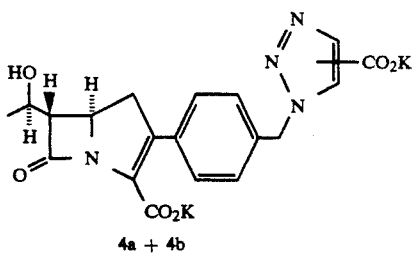

4a + 4b

Step C: Dipotassium
(5R,6S)-2-[4-(4'-carboxylate-1',2',3'-triazol-1'-ylmethyl)-phenyl]-6-[1R-hydroxyethyl]-carbapen-2-em-3-carboxylate Dipotassium
(5R,6S)-2-[4-(5'-carboxylate-1',2',3'-triazol-1'-ylmethyl)phenyl]-6-[1R-hydroxyethyl]-carbapen-2-em-3-carboxylate To a stirred solution of 77 mg (0.14 mmol) of carbapenem isomer 3a in 2.5 mL of methylene chloride and 2.5 mL of EtOAc at room temperature (RT) was added a solid mixture of triphenylphosphine (11 mg, 0.042 mmol and tetrakis(triphenylphosphine)-palladium (14 mg, 0.012 mmol). A solution of 0.5M potassium 2-ethylhexanoate in EtOAc (0.62 mL, 0.31 mmol) and 25 1 2-ethylhexanoic acid (0.16 mmol) were then added, and the reaction mixture was stirred 2 hours at room temperature. The mixture was then concentrated under a $N_2$ stream and then under vacuum. The solid was slurried in ether, and the mixture was centrifuged. The supernatant was decanted and the ether addition/centrifuge procedure repeated twice. The solid residue was then purified by RPS-F silica gel thin layer chromatography (2-1000μ plates; 2.5% EtOH in $H_2O$) to provide 33 mg (50% yield) of the title compound 4a as a white lyophilizate.

$^1$H-NMR (300 MHz, $D_2O$): δ1.28 (d, J=6 Hz, $CH_3CHO$—), 3.03 (dd, J=10, 18 Hz, $H_{1a}$), 3.40 (dd, J=8, 18 Hz, $H_{1b}$), 3.50 (dd, J=3, 6 Hz, $H_6$), 4.17–4.32 (m, $H_5$ and $CH_3CH$), 5.6 (s, —$CH_2$—triazole), 7.26 and 7.34 (2d, phenyl protons), 8.23 ppm (s, triazole proton).

UV ($H_2O$): $\lambda_{max}$=301 nm ($\epsilon$=13,000).

Employing the procedure described above, but substituting the carbapenem isomer 3b from Example 1, Step B for the carbapenem isomer 3a provided the other regioisomer 4b.

$^1$H-NMR (300 MHz, $D_2O$): δ1.27 (d, J=6 Hz, $CH_3CHO$—), 3.02 (dd, J=10, 18 Hz, $H_{1a}$), 3.38 (dd, J=9, 18 Hz, $H_{1b}$), 3.47 (dd, J=2, 6 Hz, $H_6$), 4.17–4.29 (m, $H_5$ and $CH_3CH$), 5.90 (s,—$CH_2$—triazole), 7.15, 7.30 (2d, phenyl protons), 7.98 ppm (s, triazole proton).

UV ($H_2O$): $\lambda_{max}$=301 ($\epsilon$=12,000).

EXAMPLE 2

Potassium
(5R,6S)-2[4-(4'-azidomethyl-1',2',3'-triazol-1'-ylmethyl)phenyl]-6-[1R-hydroxyethyl]-carbapen-2-em-3-carboxylate and Potassium
(5R,6S)-2-[4-(5'-azidomethyl-1',2',3'-triazol-1'-ylmethyl)phenyl]-6-[1R-hydroxyethyl]-carbapen-2-em-3-carboxylate

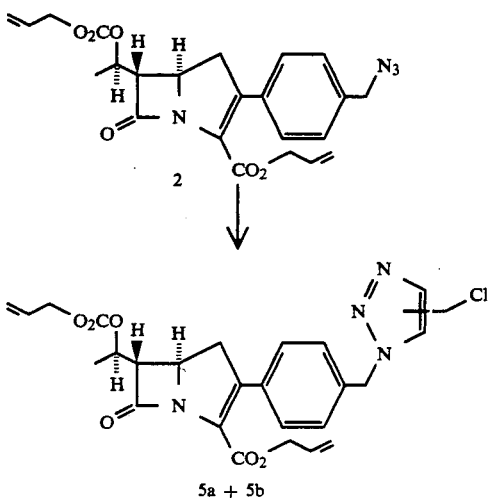

Step A: Allyl
(5R,6S)-2-[4-(4'-chloromethyl-1',2',3'-triazol-1'-ylmethyl)phenyl]-6-[1R-(allyloxycarbonyloxy)ethyl]carbapen-2-em-3-carboxylate and Allyl
(5R,6S)-2-[4-(5'-chloromethyl-1',2',3'-triazol-1'-ylmethyl)phenyl]-6-[1R-(allyloxycarbonyloxy)ethyl]carbapen-2-em-3-carboxylate A solution of carbapenem 2 from Example 1, Step A (154 mg, 0.34 mmol) and propargyl chloride (430 μL, 5.9 mmol) in 860 μL of toluene was heated in a sealed tube at 90° C. for 5 hours. The reddish brown solution was then concentrated under a nitrogen stream, and the residue was dissolved in $CH_2Cl_2$. The solution was again concentrated and the residue purified by thin layer chromatography (4-1000μ silica gel plates, 15% EtOAC in $CH_2Cl_2$) to provide two products carbapenem 5a (65 mg, 36% yield) and carbapenem 5b (38 mg, 21% yield).

5a $^1$H-NMR (300 MHz, $CDCl_3$): δ1.49 (d, J=6 Hz, $CH_3CHO$—), 3.17 (dd, $H_{1a}$), 3.28 (dd, $H_{1b}$), 3.42 (dd, $H_6$), 4.28 (m, $H_5$), 4.58-4.74 (m, $CO_2CH_2$), 4.68 (s on top of previous m, $CH_2Cl$), 5.10-5.38 (m, $CH_3CHO$ and $CH=CH_2$), 5.50 (s, phenyl-$CH_2$-triazole), 5.79-6.00 (m, $CH=CH_2$), 7.24, 7.37 (2d, phenyl protons), 7.51 ppm (s, triazole proton). p IR ($CH_2Cl_2$): 1780 (β-lactam carbonyl); 1750 and 1730 (other carbonyls)cm$^{-1}$.

5b $^1$H-NMR (300 MHz, $CDCl_3$): δ1.49 (d, J=6 Hz, $CH_3CHO$—), 3.16 (dd, J=10, 18 Hz, $H_{1a}$), 3.28 (dd, J=8, 18 Hz, $H_{1b}$), 3.41 (dd, 2.5, 8 Hz, $H_6$), 4.27 (m, $H_5$), 4.43 (s, $CH_2Cl$), 4.58-4.75 (m, $CO_2CH_2$), 5.10-5.38 (m, $CH_3CHO$ and $CH=CH_2$), 5.66 (s, phenyl-$CH_2$-triazole), 5.78-6.00 (m, $CH=CH_2$), 7.20 and 7.36 (2d, phenyl protons), 7.70 ppm (s, triazole proton).

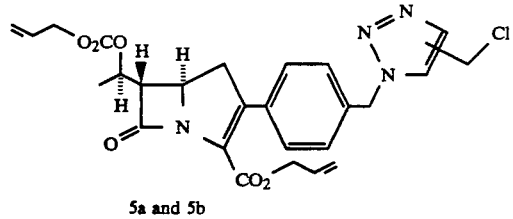

5a and 5b

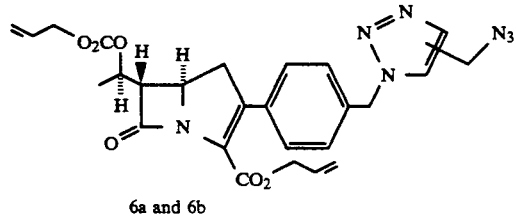

6a and 6b

Step B: Allyl
(5R,6S)-2-[4-(4'-azidomethyl-1',2',3'-triazol-1'-ylmethyl)phenyl]-6-[1R-(allyloxycarbonyloxy)ethyl]carbapen-2-em-3-carboxylate and Allyl (5R,6S)-2-[4-(5'-azidomethyl-1', 2',3'-triazol-1'-ylmethyl)phenyl]-6-[1R-(allyloxycarbonyloxy)ethyl]carbapen-2-em-3-carboxylate Lithium azide (2.1 mg, 0.042 mmol) was added to a solution of carbapenem 5a (19 mg, 0.036 mmol) in 250 μL of dimethylsulfoxide (DMSO), and the mixture was stirred 24 hours at room temperature. The reaction mixture was then partitioned between methylene chloride and $H_2O$. The separated organic layer was washed twice with brine, dried and filtered. The organic solution was concentrated under a nitrogen stream and then under vacuum. The residue was purified by thin layer chromatography (1-1000μ silica gel plate, 10% EtOAc in methylene chloride) to provide 12.8 mg (66% yield) of carbapenem 6a.

$^1$H NMR (200 MHz, $CDCl_3$): δ1.49 (d, J=6 Hz, $CH_3CHO$—), 3.18 (overlapping dd, J=10, 18 Hz, $H_{1a}$), 3.31 (overlapping dd, J=9, 18 Hz, $H_{1b}$), 3.45 (dd, J=3, 8 Hz, $H_6$), 4.30 (m, $H_5$); 4.50 (s, $CH_2N_3$), 4.58-4.79 (m, $CO_2CH_2$), 5.08-5.47 (m, $CH_3CHO$ and $CH=CH_2$); 5.56 (s, phenyl—$CH_2$—triazole); 5.79-6.06 (m, $CH=CH_2$); 7.27 and 7.41 (2d, phenyl protons), 7.51 ppm (s, triazole proton)

IR($CH_2Cl_2$) 2090($N_3$), 1780(β-lactam carbonyl); 1750 and 1725(other carbonyls) cm$^{-1}$.

Employing the procedure described above, but substituting the carbapenem isomer 5b from Example 2, Step B for the carbapenem isomer 5a provided the other regioisomer 6b. An ene-lactam by-product is observed in both the NMR and IR spectra.

$^1$H-NMR (300 MHz, $CDCl_3$): δ1.47 (d, J=6 Hz, $CH_3CHO$—), 3.15 (dd, J=10, 18 Hz, $H_{1a}$), 3.26 (dd, J=9, 18 Hz, $H_{1b}$), 3.40 (dd, J=3, 8 Hz, $H_6$), 4.27 (s, $CH_2N_3$), 4.55-4.73 (m, $CO_2CH_2$), 5.03-5.43 (m, $CH_3CHO$ and $CH=CH_2$); 5.60 (s, phenyl—$CH_2$— triazole); 5.77–5.99 (m, CH=CH₂); 7.23 and 7.35 (2d, phenyl protons), 7.70 ppm (s, triazole proton)

IR(CH₂Cl₂): 2075(N₃), 1770(β-lactam carbonyl); 1725 and 1710(other carbonyls) cm⁻¹.

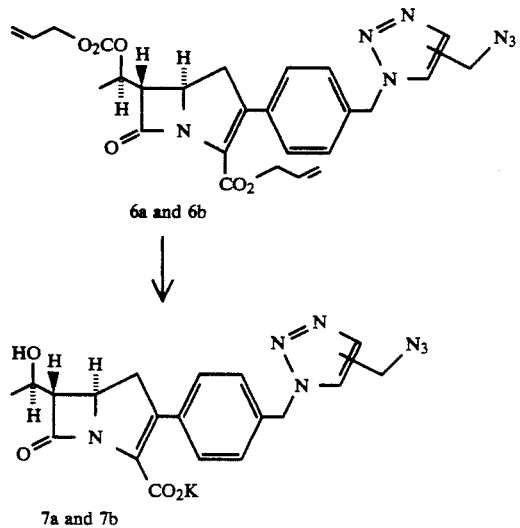

6a and 6b

↓

7a and 7b

Step C: Potassium
(5R,6S)-2-[4-(4'-azidomethyl-1',2',3'-triazol-1'-ylmethyl)phenyl]-6-1R-hydroxyethyl carbapen-2-em-3-carboxylate and Potassium
(5R,6S)-2-[4-(5'-azidomethyl-1',2',3'-triazol-1'-ylmethyl)phenyl]-6-[1R-hydroxyethyl]-carbapen-2-em-3-carboxylate To a solution of carbapenem 6a (12.8 mg, 0.024 mmol) in 0.44 mL of CH₂Cl₂ and 0.44 mL EtOAc was added 2.4 mg (0.002 mmol) of tetrakis (triphenylphosphine) palladium and 2.0 mg (0.008 mmol) of triphenyl phosphine. A 0.5M solution of potassium 2-ethyl-hexanoate in EtOAc (52 μL, 0.026 mmol) and 2-ethyl hexanoic acid (4.1 μL, 0.026 mmol) were then added, and the mixture was stirred at room temperature for 2 hours. The reaction mixture was then concentrated under a nitrogen stream, then under vacuum, and the residue was slurried in Et₂O. The slurry was centrifuged, and the supernatant was decanted. The Et₂O insoluble residue was dissolved in H₂O and purified by reverse phase thin layer chromatography (1–500μ RPS-F plate, 10% EtOH in H₂O) to provide 4 mg (35% yield) of carbapenem 7a. No ene-lactam by-product is observed by NMR.

¹H-NMR (300 MHz, D₂O): 1.27 (d, J=6 Hz, CH₃CHO—), 3.01 (dd, J=10, 18 Hz, H₁ₐ), 3.38 (dd, J=8, 18 Hz, H₁ᵦ), 3.46 (dd, J=3, 6 Hz, H₆), 4.16–4.28 (m, H₅ and CH₃CHO—), 4.46 (s, CH₂N₃), 5.58 (s, phenyl-CH₂-triazole), 7.24, 7.32 (2d, phenyl protons), 8.01 ppm (s, triazole proton). UV (H₂O) : λ_max=300nm (ε=11,500)

Employing the procedure described above, but substituting the carbapenem isomer 6b from Example 2, Step B for the carbapenem isomer 6a provided the other regioisomer 7b.

¹H-NMR (300 MHz, D₂O): 1.26 (d, J=6 Hz, CH₃CHO—), 3.01 (dd, J=10, 18 Hz, H₁ₐ), 3.38 (dd, J=8, 18 Hz, H₁ᵦ), 3.46 (dd, J=2, 6 Hz, H₆), 4.16–4.28 (m, H₅ and CH₃CHO—), 4.51 (s, CH₂N₃), 5.64 (s, phenyl-CH₂-triazole), 7.15, 7.31 (2d, phenyl protons), 7.82 ppm (s, triazole proton). UV (H₂O) : λ_max=301nm (ε=10,000).

EXAMPLE 3

Potassium (5R, 6S)-2-[4-(4'- or 5'-aminomethyl-1',2', 3'-triazol-1'-ylmethyl)phenyl]-6-[1R-hydroxyethyl]-carbapen-2-em-3-carboxylate

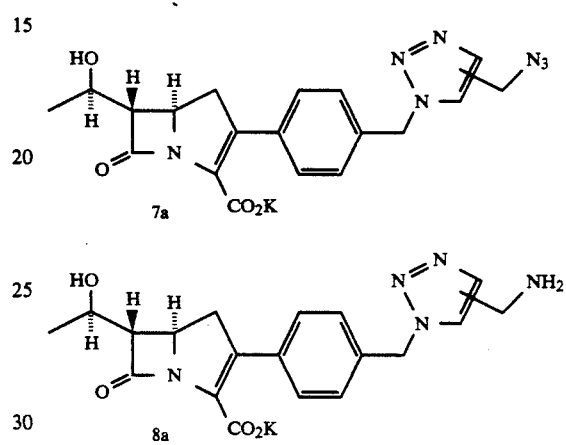

A mixture of carbapenem 7a from Example 2, Step C (7.5 mg, 0.017 mmol) and 1.5 mg 10% palladium on carbon (Pd/C) in 2 mL of D₂O and 0.34 mL of 0.1M pH7 phosphate buffer was stirred under a H₂ atmosphere (balloon pressure) for 1 hour. The system was then purged, and another 1.5 mg charge of 10% Pd/C was added. The mixture was again stirred under a H₂ atmosphere for 1 hour. The system was then purged with N₂, and the mixture was centrifuged. The supernatant was filtered through a millipore filter disk and the residue rinsed twice with H₂O. The filtrates were concentrated and purified by reverse phase thin layer chromatography (1–500μ RPS-F plate, 10% EtOH in H₂O ) to provide 1.7 mg (24% yield) of carbapenem 8a.

¹H-NMR (300 MHz, D₂O): 1.28 (d, J=6 Hz, CH₃CHO—), 3.02 (dd, J=10, 19 Hz, H₁ₐ), 3.39 (dd, J=8, 19 Hz, H₁ᵦ), 3.47 (br dd, H₆), 4.18–4.28 (m, CH₂NH₂, H₅ and CH₃CHO—, 5.60 (phenyl-CH₂-triazole), 7.26, 7.34 (2d, phenyl protons), 8.06 ppm (br. s, triazole proton).

UV (H₂O) λ_max=300nm (ε=12,000)

EXAMPLE 4

Potassium (5R,6S)-[4-(4'-hydroxymethyl-1',2',3'-triazol-1'-ylmethyl)phenyl-6-[1'-hydroxyethyl]-carbapen-2-em-3-carboxylate and Potassium (5R,6S)-[4-(5'-hydroxymethyl-1',2',3'-triazol-1'-ylmethyl)phenyl-6-[1R-hydroxyethyl]-carbapen-2-em-3-carboxylate

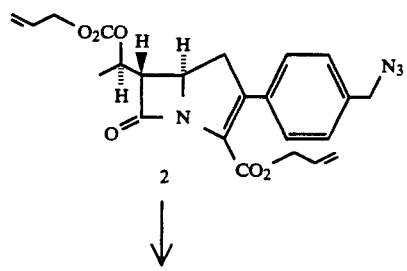

2

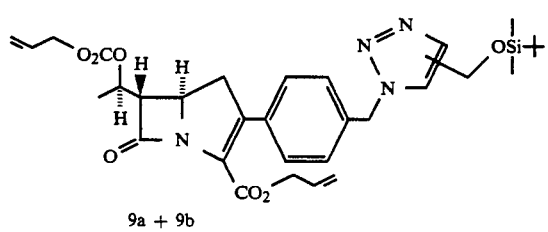

9a + 9b

Step A: Allyl (5R,6S)-2-[4-(4'-(t-butyldimethylsilyloxymethyl)-1',2',3'-triazol-1'-yl-methyl)phenyl]-6-[1R-(allyloxycarbonyloxy)ethyl]-carbapen-2-em-3-carboxylate and Allyl-(5R,6S)-2-[4-(5'-(t-butyldimethylsilyloxymethyl)-1',2',3'-triazol-1'-ylmethyl)phenyl]-6-[1R-(allyloxycarbonyloxy)ethyl]carbapen-2-em-3-carboxylate A solution of carbapenem 2 (prepared as described in Example 1) (85 mg, 0.19 mmol) and 3-(t-butyldimethylsilyloxy)propyne (240 µL, 1.41 mmol) in 470 µL of toluene was heated in a sealed tube at 70° C. for 1 hour. The cooled solution was analyzed by thin layer chromatography, which showed that the reaction was incomplete. An additional 450 µL of the propyne was added in two portions, and the reaction solution was heated a total of 10 hours at 80° C. The solution was then cooled and concentrated under vacuum. The residue was purified by thin layer chromatography (2–1000µ silica gel plates, 1:1;EtOAc:hexanes) to provide a mixture of carbapenems 9a and 9b (45 mg, 38% yield).

$^1$H-NMR (300 MHz, CDCl$_3$): δ0.05, 0.1 (2s, Si(CH$_3$)$_3$), 0.89, 0.91 (2s, C(CH$_3$)$_3$), 1.49 (d, J=6 Hz, CH$_3$CHO—), 3.11-3.22 (2dd, J=10, 18 Hz, 2×H$_{1a}$), 3.22-3.32 (2dd, J=9, 18 Hz, 2×H$_{1b}$), 3.39-3.44 (2t, 2×H$_6$), 4.23-4.32 (m, 2×H$_5$), 4.55-4.74 (m, CO$_2$CH$_2$), 4.59 (s, CH$_2$OSi of one regioisomer), 4.83 (s, CH$_2$OSi of other regioisomer), 5.07-5.39 (m, CH$_3$CHO—and CH=CH$_2$), 5.52 (s, phenyl-CH$_2$-triazole of major isomer), 5.62 (s, phenyl-CH$_2$-triazole of minor isomer), 5.78-6.00 (m, CH=CH$_2$), 7.17-7.37 (4d, phenyl protons), 7.43, 7.57 ppm (2s, triazole protons).

IR (CH$_2$Cl$_2$): 1780 (β-lactam carbonyl); 1740 and 1725 (other carbonyls) cm$^{-1}$.

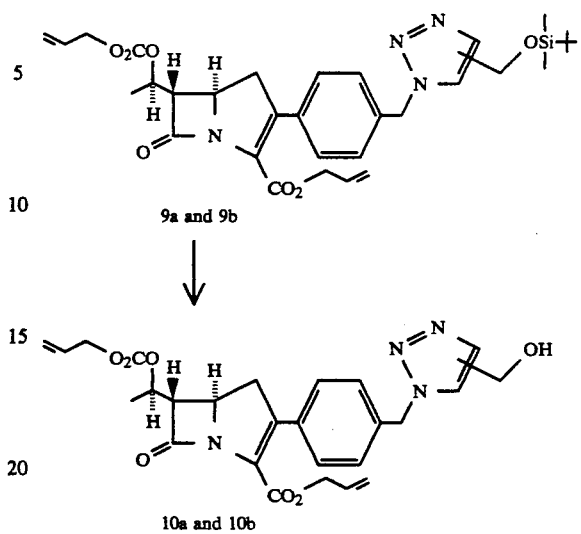

9a and 9b 10a and 10b

Step B: Allyl-(5R,6S)-2-[4-(4'-(hydroxymethyl)-1',2',3'-triazol-1'-ylmethyl)phenyl]-6-[1R-(allyloxycarbonyloxy)ethyl]-carbapen-2-em-3-carboxylate and Allyl-(5R,6S)-2-[4-(5'-(hydroxymethyl)-1',2',3'-triazol-1'-ylmethyl)phenyl]-6-[1R-(allyloxycarbonyloxy)ethyl]-carbapen-2-em-3-carboxylate Acetic acid (6 µL, 0.10 mmol) and a 1N solution of tetrabutylammonium fluoride in THF (35 µL, 0.035 mmol) were added to a solution of 22 mg (0.035 mmol) of the mixture of regioisomeric carbapenems 9a and 9b from Step A in 0.4 mL of THF. The solution was stirred for 4.5 hours at RT and then partitioned between 0.5 mL 1N K$_2$HPO$_4$/1 mL H$_2$O/1 mL EtOAc. The layers were separated and the aqueous layer again extracted with EtOAc. The combined EtOAc layers were washed with brine, dried, filtered and concentrated under vacuum. The residue was purified by thin layer chromatography (1–500µ silica gel plate, EtOAc) to provide approximately equal quantities of the separated regioisomers, carbapenem 10a and carbapenem 10b.

10a $^1$H-NMR (300 MHz, CDCl$_3$): δ1.47 (d, J=6 Hz, CH$_3$CHO—), 3.14 (dd, J=10, 18 Hz, H$_{1a}$), 3.25 (dd, J=9, 18 Hz, H$_{1b}$), 3.39 (dd, J=3, 8 Hz, H$_6$), 4.26 (m, H$_5$), 4.54-5.38 (m, CO$_2$CH$_2$), 4.6 (s, CH$_2$OH), 5.08-5.38 (m, CH$_3$CHO—and CH=CH$_2$), 5.62 (s, phenyl-CH$_2$-triazole), 5.76-5.98 (m, CH=CH$_2$), 7.21, 7.32 (2d, phenyl protons), 7.58 ppm (s, triazole proton).

IR (CH$_2$Cl$_2$): 1780 (β-lactam carbonyl); 1740 and 1725 (other carbonyls) cm$^{-1}$.

$^1$H-NMR (300 MHz, CDCl$_3$): δ1.48 (d, J=6 Hz, CH$_3$CHO—), 3.15 (dd, J=10, 18 Hz, H$_{1a}$), 3.27 (dd, J=8, 18 Hz, H$_{1b}$), 3.40 (dd, J=3, 8 Hz, H$_6$), 4.27 (m, H$_5$), 4.57-4.80 (m, CO$_2$CH$_2$), 4.77 (s, CH$_2$OH), 5.09-5.38 (m, CH$_3$CHO—and CH=CH$_2$), 5.51 (s, phenyl-CH$_2$-triazole), 5.79-6.01 (m, CH=CH$_2$), 7.22, 7.45 (2d, phenyl protons), 7.45 ppm (s, triazole proton).

IR (CH$_2$Cl$_2$): 1780 (β-lactam carbonyl); 1750 and 1720 (other carbonyls) cm$^{-1}$.

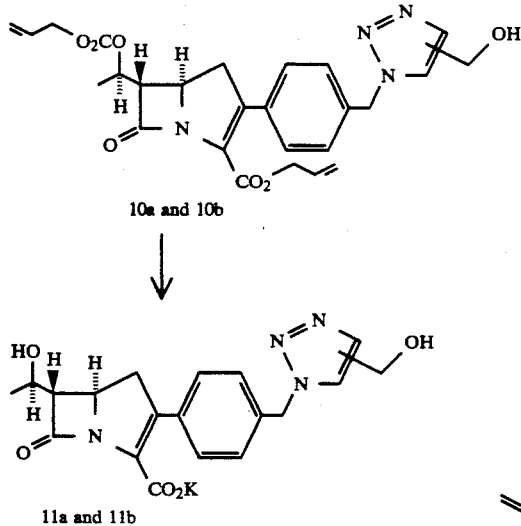

10a and 10b

↓

11a and 11b

Step C: Potassium (5R,6S)-2-[4-(4'-(hydroxymethyl)-1', 2',3'-triazol-1'-ylmethyl)phenyl]-6-[1R-hydroxyethyl]-carbapen-2-em-3-carboxylate and Potassium (5R,6S)-2-[4-(5'-(hydroxymethyl)-1',2',3'-triazol-1'-ylmethyl)phenyl]-6-[1R-hydroxyethyl]-carbapen-2-em-3-carboxylate Employing the procedure described in Example 2, Step C but substituting carbapenem 10a (prepared as described in Step B) for carbapenem 6a provided carbapenem 11a.

$^1$H-NMR (300 MHz, D$_2$O): δ1.28 (d, J=6 Hz, CH$_3$CHO—), 3.02 (dd, J=10, 18 Hz, H$_{1a}$), 3.39 (dd, J=8, 18 Hz, H$_{1b}$), 3.47 (m, H$_6$), 4.18–4.29 (m, H$_5$ and CH$_3$CHO—), 4.65 (s, CH$_2$O H), 5.63 (s, phenyl—CH$_2$—triazole), 7.15 and 7.32 (2d, phenyl protons), 7.76 ppm (s, triazole proton)

UV (H$_2$O): λ$_{max}$=302 nm

Employing the procedure described in Example 2, Step C but substituting carbapenem 10b (prepared as described in Step B) for carbapenem 6a, and using 8% CH$_3$CN in H$_2$O as the chromatography eluant, provided carbapenem 11b.

$^1$H-NMR (300 MHz, D$_2$O): δ1.30 (d, J=6 Hz, CH$_3$CHO—), 3.05 (dd, J=11, 17 Hz, H$_{1a}$), 3.42 (dd, J=8, 17 Hz, H$_{1b}$), 3.49 (dd, J=3, 6 Hz, H$_6$), 4.10–4.32 (m, H$_5$ and CH$_3$CHO—), 4.68 s, CH$_2$O H), 5.60 (s, phenyl—CH$_2$—triazole), 7.26 and 7.36 (2d, phenyl protons), 7.97 ppm (s, triazole proton)

UV (H$_2$O): λ$_{max}$=302 nm

EXAMPLE 5

(5R,6S)-2-[4-(4'-N-Pyridinium methyl-1',2',3'-triazol-1'-ylmethyl)phenyl]-6-[1R-hydroxyethyl]-carbapen-2-em-3-carboxylate (5R,6A)-2-[4-(5'-N-Pyridinium methyl-1',2',3'-triazol-1'-ylmethyl)phenyl]-6-[1R-hydroxyethyl]-carbapen-2-em-3-carboxylate

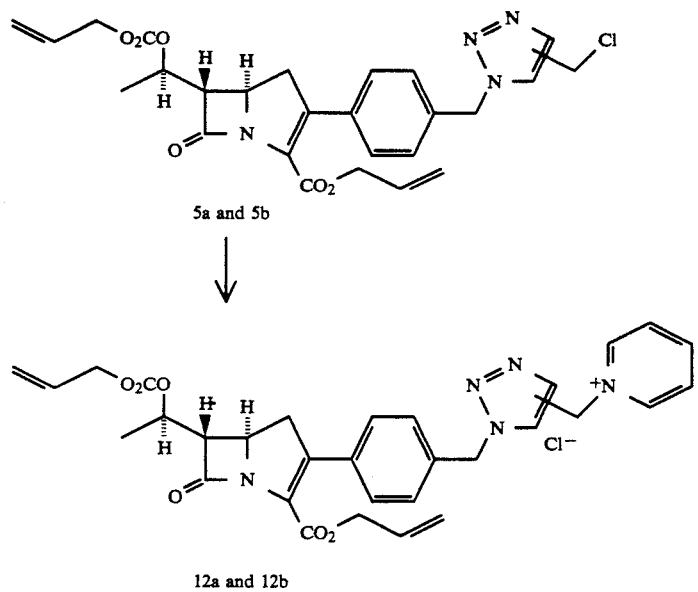

5a and 5b

↓

12a and 12b

Step A: Allyl (5R,6S)-2-[4-(4'-N-pyridinium methyl-1',2',3'-triazol-1'-ylmethyl)phenyl]-6-[1R-(allyloxycarbonyloxy)-ethyl]carbapen-2-em-3-carboxylate chloride . and Allyl (5R,6S)-2-[4-(5'-N-pyridiniummethyl-1',2',3'-triazol-1'-ylmethyl)phenyl]-6-[1R-(allyloxycarbonyloxy)-ethyl]-carbapen-2-em-3-carboxylate chloride A solution of carbapenem 5a (prepared as described in Example 2, Step A) (58 mg, 0.11 mmol) and pyridine (100 μl, 1.24 mmol) in 1 mL of acetonitrile was heated at 90° C. under a N$_2$ atmosphere for 90 minutes. Another 0.9 mL (11 mmol) of pyridine was added, and the solution was heated for another 3.5 hours. The solution was then cooled and concentrated under vacuum. The residue was purified by thin layer chromatography (2–1000μ silica gel plates, 20% methanol in methylene chloride) to provide 13.6 mg (21% yield) of carbapenem 12a.

$^1$H-NMR (300MHz, CDCl$_3$): δ1.41 (d, CH$_3$CHO—), 3.09 (dd, H$_{1a}$) 3.22 (dd, H$_{1b}$), 3.36 (dd, H$_6$), 4.21 (m, H$_5$), 4.50–4.65 (m, CO$_2$CH$_2$), 5.03–5.31 (m, CH$_3$CHO—and CH=CH₂), 5.42 (s, phenyl—CH₂—triazole), 5.71–5.93 (m, CH=CH₂), 6.39 (s, CH₂-pyridinium), 7.20, 7.27 (2d, phenyl protons), 7.93(t), 8.32(t), and 9.76(d) (pyridinium protons), 8.74 ppm(s, triazole proton).

IR (CH₂Cl₂): 1775(β-lactam carbonyl); 1735 and 720(other carbonyls) cm¹.

Employing the procedure described above, but substituting the carbapenem isomer 5b from Example 2, Step A for the carbapenem isomer 5a provided the other regioisomer 12b.

¹H-NMR (300MHz, CDCl₃): δ1.40 (d, J=6 Hz, CH₃CHO—), 2.96 (dd, J=10 and 18 Hz, H₁ₐ) 3.15 (dd, J=9 and 18 Hz, H₁ᵦ), 3.35 (dd, J=2 and 8 Hz, H₆), 4.17 (m, H₅), 4.48–4.72 (m, CO₂CH₂), 5.02–5.44 (m, CH₃CHO—and CH=CH₂), 5.18 (s, phenyl—CH₂—triazole), 5.77–5.94 (m, CH=CH₂), 6.13 (broad s, CH₂—pyridinium), 6.92 (broad s, phenyl protons), 7.58 (broad s), 7.98 (broad d), and 9.10 (broad s) (pyridinium protons), 8.19 ppm(s, triazole proton). (minor impurities from other regioisomer appear in the spectrum)

IR (CH₂Cl₂): 1780(β-lactam carbonyl); 1740 and 1715(other carbonyls) cm⁻¹.

Employing the procedure described in Example 2, Step C, but substituting carbapenem 12b from Step A for carbapenem 6a and using 25% CH₃CN in H₂O as the chromatography eluant, provided carbapenem 13b.

¹H-NMR (300 MHz, D₂O): δ1.30 (d, J=6 Hz, CH₃CHO—), 2.99 (dd, J=10, 16 Hz, H₁ₐ), 3.31 (dd, J=8, 16 Hz, H₁ᵦ), 3.49 (dd, J=3, 6 Hz, H₆), 4.20–4.33 (m, H₅, CH₃CHO—) 5.80 (s, phenyl—CH₂—triazole), 6.00 (s, CH₂—pyridinium) 6.77 and 7.06 (2d, phenyl protons), 7.73 (t), 8.36 (t), and 8.45 (d)(pyridinium protons), 8.23 ppm (s, triazole proton).

UV (H20): λ$_{max}$=301 nm; sl. shoulder at 260 nm.

EXAMPLES 6–53

The following examples are prepared by a method analogous to that described in Examples 1–4 using the appropriate starting materials readily available or readily prepared by techniques known in the art. It is understood that in the synthesis of the following examples protecting groups known in the art may need to be employed. It is also understood that synthesis of an example compound may require functional group ma-

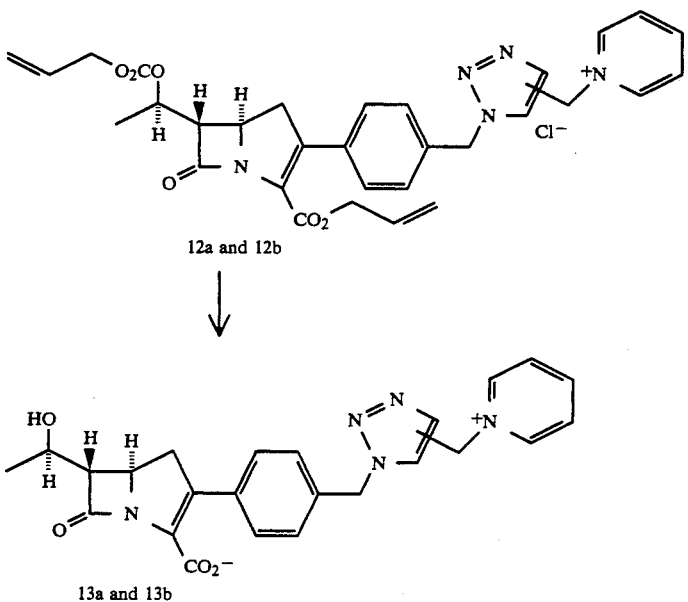

12a and 12b

↓

13a and 13b

Step B: (5R, 6S)-2-[4-(4′-N-Pyridiniummethyl-1′,2′,3′-triazol-1′-ylmethyl)phenyl-6-[1R-hydroxyethyl]-carbapen-2-em-3-carboxylate and (5R, 6S)-2-[4-(5′-N-Pyridiniummethyl-1′,2′,3′-triazol-1′-ylmethyl)phenyl]-6-(1R-hydroxyethyl)-carbapen-2-em-3-carboxylate Employing the procedure described in Example 2, Step C, but substituting carbapenem 12a from Step A for carbapenem 6a and using 25% CH₃CN in H₂O as the chromatography eluant, provided carbapenem 13a.

¹H-NMR (300MHz, D₂O): δ1.29 (d, J=6 Hz, CH₃CHO—), 3.03 (dd, J=10, 17 Hz, H₁ₐ), 3.40 (dd, J=8, 17 Hz, H₁ᵦ), 3.48 (dd, J=3, 6 Hz, H₆), 4.19–4.31 (m, H₅, CH₃CHO—) 5.62 (s, phenyl—CH₂—triazole), 5.93 (s, CH₂—pyridinium) 7.27 and 7.34 (2d, phenyl protons), 8.06 (t), 8.55 (t), and 8.90 (d)(pyridinium protons), 8.25 ppm (s, triazole proton).

nipulation well known in the art.

| EXAMPLE | R$^c$ |
|---------|-------|
| 6 | 4-CH₂NH₂ |
| 7 | 5-CH₂NH₂ |
| 8 | 4-CH₂Cl |
| 9 | 5-CH₂Cl |
| 10 | 4-CH₂Br |
| 11 | 5-CH₂Br |
| 12 | 4-CH₂OC(O)NH₂ |
| 13 | 5-CH₂OC(O)NH₂ |
| 14 | 4-CHO |
| 15 | 5-CHO |
| 16 | 4-CN |

-continued

| EXAMPLE | R$^c$ |
|---|---|
| 17 | 5-CN |
| 18 | 4-CH=NOH |
| 19 | 4-CH$_2$I |
| 20 | 5-CH$_2$I |
| 21 | 4-CO$_2$CH$_3$ |
| 22 | 5-CH=NOH |
| 23 | 4-C(O)NH$_2$ |
| 24 | 5-C(O)NH$_2$ |
| 25 | 4-C(O)CH$_3$ |
| 26 | 5-C(O)CH$_3$ |
| 27 | 4-CH$_2$SCH$_3$ |
| 28 | 5-CH$_2$SCH$_3$ |
| 29 | 4-CH$_2$S(O)CH$_3$ |
| 30 | 5-CH$_2$S(O)CH$_3$ |
| 31 | 4-CH$_2$S(O)$_2$CH$_3$ |
| 32 | 5-CH$_2$S(O)$_2$CH$_3$ |
| 33 | 4-CH$_2$NHC(NH)H |
| 34 | 5-CH$_2$NHC(NH)H |
| 35 | 4-CH$_2$OCH$_3$ |
| 36 | 5-CH$_2$OCH$_3$ |
| 37 | 5-CO$_2$CH$_3$ |

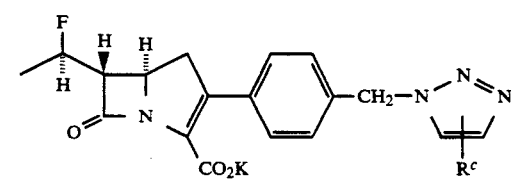

| 38 | 4-CH$_2$NH$_2$ |
| 39 | 5-CH$_2$NH$_2$ |
| 40 | 4-CO$_2$K |
| 41 | 5-CO$_2$K |
| 42 | 4-CH$_2$N$_3$ |
| 43 | 5-CH$_2$N$_3$ |
| 44 | 4-CH$_2$OH |
| 45 | 5-CH$_2$OH |

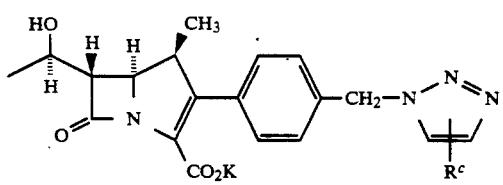

| 46 | 4-CH$_2$NH$_2$ |
| 47 | 5-CH$_2$NH$_2$ |
| 48 | 4-CO$_2$K |
| 49 | 5-CO$_2$K |
| 50 | 4-CH$_2$N$_3$ |
| 51 | 5-CH$_2$N$_3$ |
| 52 | 4-CH$_2$OH |
| 53 | 5-CH$_2$OH |

EXAMPLES 54–87

The following examples are prepared by a method analogous to that described in Examples 5 using the appropriate starting materials readily available or readily prepared by techniques known in the art. It is understood that in the synthesis of the following examples protecting groups known in the art may need to be employed. It is also understood that synthesis of an example compound may require functional group manipulation well known in the art.

| EXAMPLE | R$^c$ |
|---|---|
| | 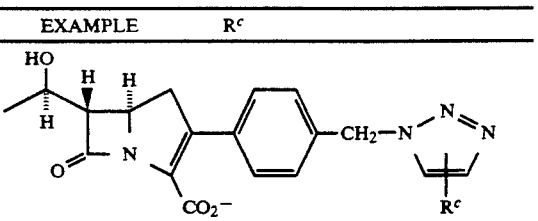 |
| 54 | 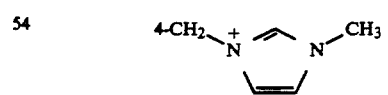 |
| 55 | 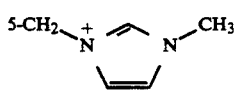 |
| 56 | 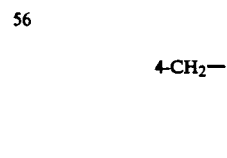 |
| 57 | 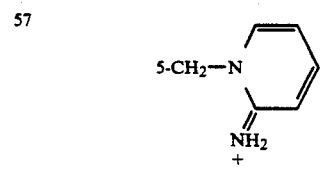 |
| 58 | 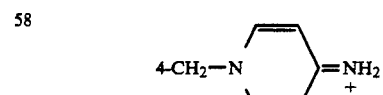 |
| 59 | 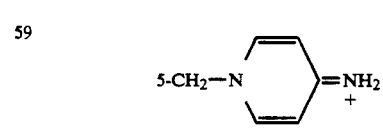 |
| 60 | 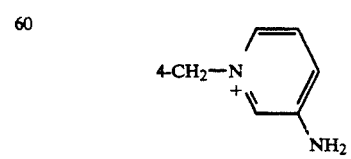 |
| 61 | 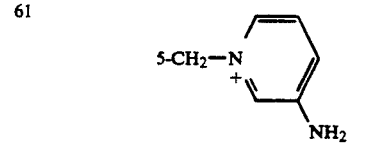 |
| 62 | 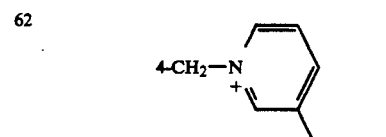 |
| 63 |  |

-continued

| EXAMPLE | R^c |
|---|---|

Structure (Example 35 header compound): carbapenem with fluoroethyl side chain, attached to phenyl-CH2-N-triazole with R^c substituent; carboxylate.

| EXAMPLE | R^c |
|---|---|
| 64 | 4-CH2-N(+)=CH-N(CH3) (N-methylimidazolium, 4-linked) |
| 65 | 5-CH2-N(+)=CH-N(CH3) (N-methylimidazolium, 5-linked) |
| 66 | 4-CH2-N(pyridine)-2-NH2 (+) (2-amino-1-pyridinium, 4-linked) |
| 67 | 5-CH2-N(pyridine)-2-NH2 (+) (2-amino-1-pyridinium, 5-linked) |
| 68 | 4-CH2-N(pyridine)=NH2 (+) at 4-position (4-iminopyridinium, 4-linked) |
| 69 | 4-CH2-N(+)(pyridinium), 4-linked |
| 70 | 5-CH2-N(pyridine)=NH2 (+) (4-iminopyridinium, 5-linked) |
| 71 | 4-CH2-N(+)(pyridinium)-3-NH2 |
| 72 | 5-CH2-N(+)(pyridinium)-3-NH2 |
| 73 | 4-CH2-N(+)(pyridinium)-CH2SCH3 |
| 74 | 5-CH2-N(+)(pyridinium)-CH2SCH3 |
| 75 | 5-CH2-N(+)(pyridinium) |

Structure (Example 36 header compound): carbapenem with 1-hydroxyethyl and methyl substituents, attached to phenyl-CH2-N-triazole with R^c substituent; carboxylate.

| EXAMPLE | R^c |
|---|---|
| 76 | 4-CH2-N(+)=CH-N(CH3) (N-methylimidazolium, 4-linked) |
| 77 | 5-CH2-N(+)=CH-N(CH3) (N-methylimidazolium, 5-linked) |
| 78 | 4-CH2-N(pyridine)-2-NH2 (+) (2-amino-1-pyridinium, 4-linked) |
| 79 | 5-CH2-N(pyridine)-2-NH2 (+) (2-amino-1-pyridinium, 5-linked) |
| 80 | 4-CH2-N(pyridine)=NH2 (+) (4-iminopyridinium, 4-linked) |
| 81 | 4-CH2-N(+)(pyridinium), 4-linked |
| 82 | 5-CH2-N(pyridine)=NH2 (+) (4-iminopyridinium, 5-linked) |
| 83 | 4-CH2-N(+)(pyridinium)-3-NH2 |

-continued

| EXAMPLE | $R^c$ |
|---|---|
| 84 | 5-CH$_2$—pyridinium-NH$_2$ |
| 85 | 4-CH$_2$—pyridinium-SCH$_3$ |
| 86 | 5-CH$_2$—pyridinium-SCH$_3$ |
| 87 | 5-CH$_2$—pyridinium |

What is claimed is:

1. A compound of the formula I:

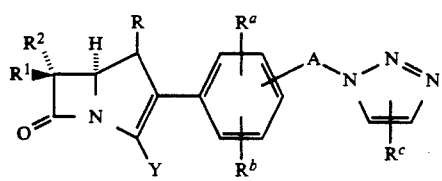

wherein:
R is H or CH$_3$;
R$^1$ and R$^2$ are independently H, CH$_3$—, CH$_3$CH$_2$—, (CH$_3$)$_2$, HOCH$_2$—, (R)—CH$_3$CH(OH)—, (CH$_3$)$_2$C(OH)—, FCH$_2$—, F$_2$CH—, F$_3$C—, (R)—CH$_3$CH(F)—, CH$_3$CF$_2$—, or (CH$_3$)$_2$C(F)—;
R$^a$ and R$^b$ are independently hydrogen or:
  a) a trifluoromethyl group: —CF$_3$;
  b) a halogen atom: —Br, —Cl, —F, or —I;
  c) C$_1$-C$_4$ alkoxy radical: —OC$_{1-4}$ alkyl, wherein the alkyl is optionally mono-substituted by R$^q$, where
R$^q$ is a member selected from the group consisting of —OH, OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono substituted by M$^a$ as defined above) and SO$_3$M$^b$ (where M$^b$ is hydrogen or an alkali metal);
  d) a hydroxy group: —OH;
  e) a carbonyloxy radical: —O(C=O)R$^2$, where
R$^s$ is C$_{1-4}$ alkyl or phenyl, each of which is optionally mono-substituted by R$^q$ as defined above;
  f) a carbamoyloxy radical: —O(C=O)N(R$^y$)R$^z$ where R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2 to 4-membered alkylidene radical, interrupted by —O, —S—, —S(O)—, —S(O)$_2$—or —NR$^e$—, to form a ring (where R$^e$ is hydrogen, C$_1$-C$_4$alkyl, and C$_1$-C$_4$alkyl mono-substituted with R$^q$ and the ring is optionally mono substituted with R$^q$ as defined above);
  g) a sulfur radical: —S(O)$_n$—R$^s$ where n=0–2, and R$^s$ is defined above;
  h) a sulfamoyl group: —SO$_2$N(R$^y$)R$^z$ where R$^y$ and R$^z$ are as defined above;
  i) azido: N$_3$
  j) a formamido group: —N(R$^t$)(C=O)H, R$^t$ is H or C$_{1-4}$ alkyl, and the alkyl thereof is optionally mono substituted by R$^q$ as defined above;
  k) a (C$_1$-C$_4$ alkyl)carbonylamino radical: —N(R$^t$)(C=O)C$_{1-4}$ alkyl, where R$^t$ is as defined above, and the alkyl group is also optionally mono substituted by R$^q$ as defined above;
  l) a (C$_1$-C$_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;
  m) a ureido group: —N(R$^t$)(C=O)N(R$^y$)R$^z$ where R$^t$, —R$^y$ and R$^z$ are as defined above;
  n) a sulfonamido group: —N(R$^t$)SO$_2$R$^s$, where R$^s$ and R$^t$ are as defined above;
  o) a cyano group —CN;
  p) a formyl or acetalized formyl radical: —(C=O)H or —CH(OCH$_3$)$_2$:
  q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;
  r) carbonyl radical: —(C=O)R$^s$, where R$^s$ is as defined above;
  s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;
  t) a (C$_1$-C$_4$ alkoxy)carbonyl radical: —(C=O)OC$_{1-4}$ alkyl, where the alkyl is optionally mono-substituted by R$^q$ as defined above;
  u) a carbamoyl radical: —(C=O)N(R$^y$)R$^z$ where R$^y$ and R$^z$ are as defined above;
  v) an N-hydroxycarbamoyl or N(C$_1$-C$_4$ alkoxy)-carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;
  w) a thiocarbamoyl group: —(C=S)N(R$^y$)R$^z$ where R$^y$ and R$^z$ are as defined above;
  x) carboxyl: —COOM$^b$, where M$^b$ is as defined above;
  y) thiocyanate: —SCN;
  z) trifluoromethylthio: —SCF$_3$;
  aa) tetrazolyl, where the point of attachment is the carbon atom of the tetrazole ring and one of the nitrogen atoms is mono substituted by hydrogen, an alkali metal or a C$_1$-C$_4$ alkyl optionally substituted by R$^q$ as defined above;

ab) an anionic function selected from the group consisting of: phosphono [P=O(OM$^b$) ]; alkylphosphono (P=O(OM$^b$)—[O(C$_1$-C$_4$ alkyl)]); alkylphosphinyl [P=O(OM$^b$)—(C$_1$-C$_4$ alkyl)]; phosphoramido [P=O(OM$^b$)N(R$^y$)R$^z$ and P=O-(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl where the phenyl is optionally monosubstituted by R$^q$, as defined above; M$^b$ is as defined above; and R$^y$ and R$^z$ are as defined above;

ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each heteroatom has both of its attached hydrogen atoms replaced by one oxygen thus forming a carbonyl moiety and there are one or two carbonyl moieties present in the ring;

ad) C$_2$-C$_4$ alkenyl radical, optionally mono-substituted by one of the substituents a) to ac) above and phenyl which is optionally substituted by R$^q$ as defined above;

ae) C$_2$-C$_4$ alkynyl radical, optionally mono-substituted by one of the substituents a) to ac) above;

af) C$_1$-C$_4$ alkyl radical;

ag) C$_1$-C$_4$ alkyl mono substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono substituted by one of the substituents a) to ag) above;

R$^c$ is

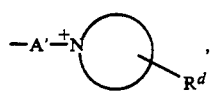

but independently selected from R$^a$ and from each other if more than one R$^c$ is present, and is attached to a ring carbon atom;

R$^d$ is R$^a$ as defined hereinabove, hydrogen or —NR$^y$R$^z$ (where R$^y$ and R$^z$ are defined hereinabove);

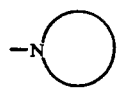

is selected from the group consisting of

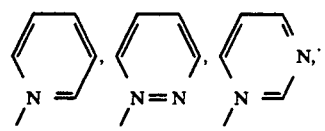

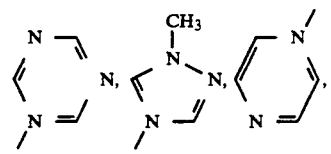

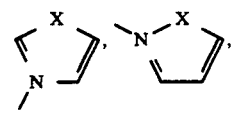

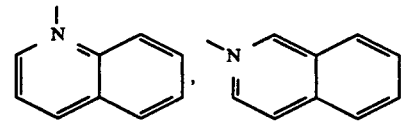

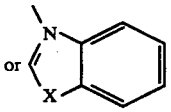

where X = O, S, or NR$_a$;
R$_a$ = Me, CH$_2$CN, CH$_2$CONH$_2$, CH$_2$CO$_2^-$ or CH$_2$SO$_3^-$.

A and A' are independently (CH$_2$)$_m$—Q—(CH$_2$)$_n$, where m is zero to 6 and n is zero to 6 and Q is a covalent bond, O, S, SO, SO$_2$, NH, —SO$_2$NH—, NHSO$_2$—, CONH—, —NHCO—, —SO$_2$N(C$_1$-C$_4$alkyl)—, —N(C$_1$-C$_4$alkyl)SO$_2$—, —CON(C$_1$-C$_4$alkyl)—, —N(C$_1$-C$_4$alkyl)CO—, —CH=CH—, —CO—, —OC(O)—, —C(O)O— or N(C$_1$-C$_4$alkyl); provided when m=n=zero that Q is not a covalent bond;

Y is selected from:
i) COOH or a pharmaceutically acceptable ester,
ii) COOM wherein M is an alkali metal, or
iii) COO$^-$;
provided that when Y is other than iv) and a quaternary nitrogen heteroatom is present, a counterion Z$^-$ is provided, or the pharmaceutically acceptable salt thereof.

2. The compound of claim 1 wherein R$^1$ is H—and R$^2$ is (R)—CH$_3$CH(OH)—or (R)—CH$_3$CH(F)—.

3. The compound of claim 1 wherein R$^a$ and R$^b$ are independently:
—H
—OCH$_2$CO$_2$Na
—OCH$_2$CH$_2$OH
—CF$_3$
—F
—Cl
—Br
—I
—OH
—OCOCH$_3$
—OCONH$_2$
—SCH$_3$
—SOCH$_3$
—SO$_2$CH$_3$
—SCH$_2$CH$_2$OH
—SOCH$_2$CH$_2$OH
—SONH$_2$ —SO₂N(CH₃)₂
—NHCHO
—NHCOCH₃
—NHCO₂CH₃
—NHSO₂CH₃
—CN
—CHO
—COCH₃
—COCH₂OH
—CH=NOH
—CH=NOCH₃
—CH=NOCH₂CO₂H
—CH=NOCMe₂CO₂H
—CH=NOCMe₂CO₂Me
—CO₂CH₂CH₂OH
—CONH₂
—CONHCH₃
—CON(CH₃)₂
—CONHCH₂CN
—CONHCH₂CONH₂
—CONHCH₂CO₂H
—CONHOH
—CONHOCH₃
—tetrazolyl
—CO₂Na
—SCF₃
—PO₃NaH
—CONHSO₂Ph
—CONHSO₂NH₂
—SO₃Na
—SO₂NHCN
—SO₂NHCONH₂
—CH=CHCN
—CH=CHCONH₂
—CH=CHCO₂Na
—C≡C—CONH₂
—C≡C—CN
—CH₂OH
—CH₂N₃
—CH₂CO₂Na
—SO₂CH₂CH₂OH
—OCH₃ or —CH₂I.

4. The compound of claim 3 wherein R¹ is H— and R² is (R)—CH₃CH(OH)— or (R)—CH₃CH(F)—.

5. The compound which is

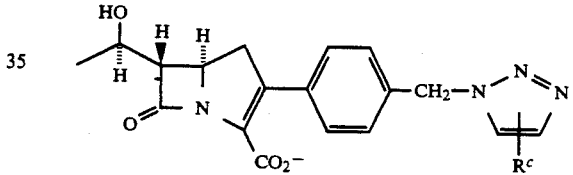

wherein Rᶜ is:

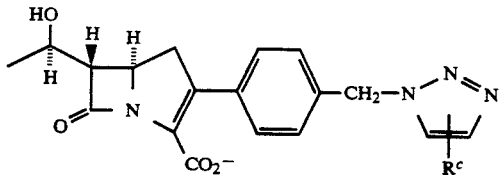

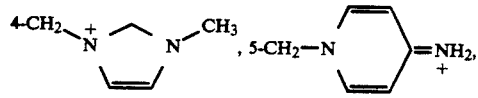

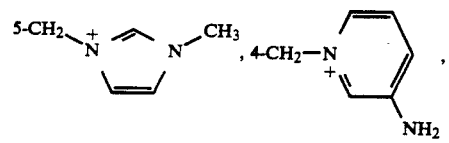

-continued

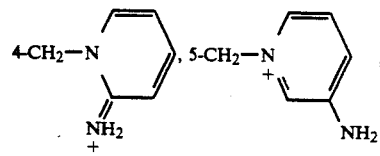

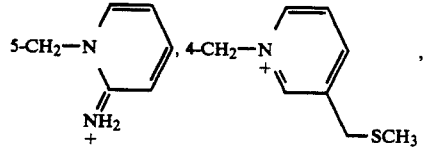

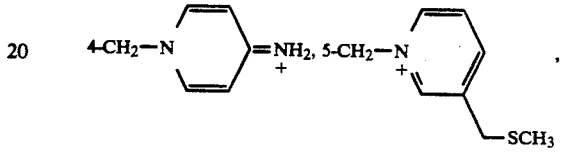

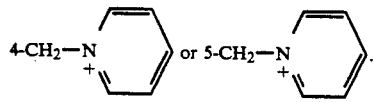

6. The compound which is

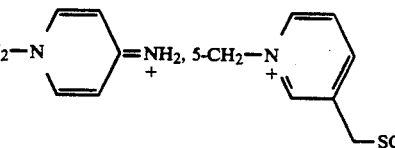

wherein Rᶜ is:

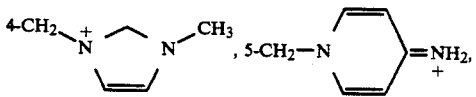

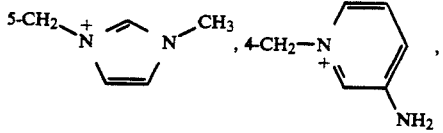

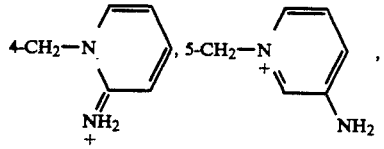

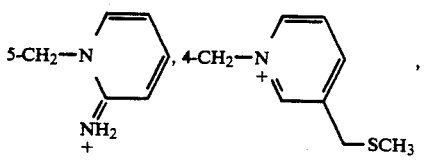

-continued

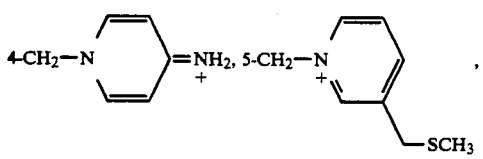

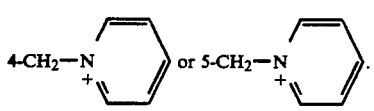

7. The compound which is

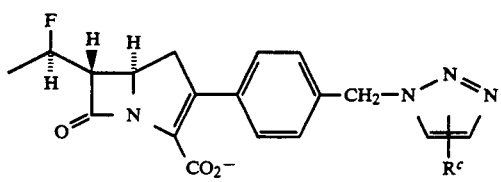

wherein R^c is:

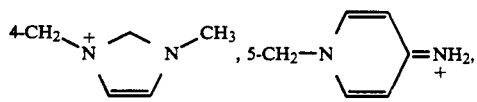

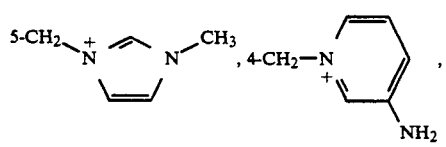

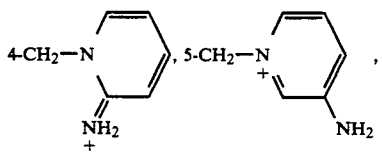

-continued

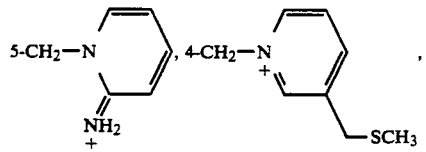

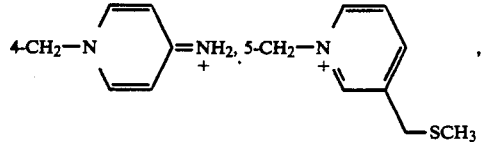

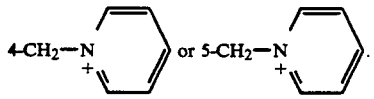

8. A pharmaceutical composition for antibacterial use comprising an antibacterially effective amount of a compound of claim 1 and a pharmaceutically acceptable carrier therefor.

9. A method of treating bacterial infections in human or animal subjects in need of such treatment comprising administering to such subject an antibacterially effective amount of a compound of claim 1.

10. A pharmaceutical composition for antibacterial use comprising an antibacterially effective amount of a compound of claim 1, an inhibitorily effective amount of a DHP inhibitor, and, optionally, a pharmaceutically acceptable carrier therefor.

11. The pharmaceutical composition according to claim 10 wherein the DHP inhibitor is 7-(L-2-amino-2-carboxyethylthio)-2-(2,2-dimethylcyclopropanecarboxamide)-2-heptenoic acid.

12. A method of treating bacterial infections in human or animal subjects in need of such treatment comprising coadministering to such subject an antibacterially effective amount of a compound of claim 1 and an inhibitorily effective amount of a DHP inhibitor.

13. The method according to claim 12 wherein the DHP inhibitor is 7-(L-2-amino-2-carboxyethylthio)-2-(2,2-dimethylcyclopropanecarboxamide)-2-heptenoic acid.

* * * * *